(12) United States Patent
Roepman et al.

(10) Patent No.: US 10,036,070 B2
(45) Date of Patent: Jul. 31, 2018

(54) METHODS AND MEANS FOR MOLECULAR CLASSIFICATION OF COLORECTAL CANCERS

(75) Inventors: Paul Roepman, Amsterdam (NL); Iris Simon, Amsterdam (NL); Tian Sun, Amsterdam (NL)

(73) Assignee: AGENDIA N.V., Amsterdam (NL)

( * ) Notice: Subject to any disclaimer, the term of this patent is extended or adjusted under 35 U.S.C. 154(b) by 0 days.

(21) Appl. No.: 13/992,020

(22) PCT Filed: Dec. 23, 2011

(86) PCT No.: PCT/NL2011/050901
§ 371 (c)(1),
(2), (4) Date: Jul. 24, 2013

(87) PCT Pub. No.: WO2012/087144
PCT Pub. Date: Jun. 28, 2012

(65) Prior Publication Data
US 2013/0296191 A1 Nov. 7, 2013

(30) Foreign Application Priority Data
Dec. 23, 2010 (EP) .................................... 10196768

(51) Int. Cl.
C12Q 1/68 (2018.01)
C12Q 1/6886 (2018.01)
(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/158* (2013.01)
(58) Field of Classification Search
CPC .................................................. C12Q 1/6886
USPC .......................................................... 506/9
See application file for complete search history.

(56) References Cited

U.S. PATENT DOCUMENTS

| 6,204,375 | B1 | 3/2001 | Lader | |
|---|---|---|---|---|
| 7,138,226 | B2 | 11/2006 | Vincek et al. | |
| 2004/0265230 | A1* | 12/2004 | Martinez et al. | 424/1.49 |
| 2007/0231822 | A1* | 10/2007 | Mitas | 435/6 |
| 2008/0070797 | A1* | 3/2008 | Mounts | C12Q 1/6837 506/9 |
| 2009/0297506 | A1* | 12/2009 | Orntoft | C12Q 1/6886 424/133.1 |

FOREIGN PATENT DOCUMENTS

| DE | 10021390 | | 11/2001 | |
|---|---|---|---|---|
| EP | 2177615 | | 4/2010 | |
| EP | 2202320 | | 6/2010 | |
| WO | 2004083369 | | 9/2004 | |
| WO | WO 2009002175 | A1 * | 12/2008 | |
| WO | WO 2009098197 | A1 * | 8/2009 | G01N 33/5023 |
| WO | WO 2010040571 | A2 * | 4/2010 | |
| WO | 2010074573 | | 7/2010 | |
| WO | WO 2010074573 | A1 * | 7/2010 | |
| WO | 2010/101916 | | 9/2010 | |
| WO | WO 2010120914 | A1 * | 10/2010 | C12Q 1/6809 |
| WO | WO 2011068839 | A1 * | 6/2011 | |
| WO | WO 2011144718 | A2 * | 11/2011 | |

OTHER PUBLICATIONS

Agilent GeneList, Agilent GeneList 44K, 2007, 1-9.*
Score Results; 20150501_1720732_us_13-992-020-020a-6.rng, 2015, 1-40.*
Score Results; 20150501_075704_us-13-992-020a-2.rng, 2015, 1-51.*
Lanza et al., mRNA/microRNA Gene Expression Profile in Microsatellite Unstable Colorectal Cancer, 2007, 6(54), 1-11.*
Vilar et al., Microsatellite Instability in Colorectal Cancer—The Stable Evidence, Nature Reviews, Clinical Oncology, 2010, 1-10.*
Hintze, C., Chapter 120, Agilent TXT File Pre-Processing Engine, User's Guide I: Quick Start, Introduction, Importing Microarray Data, Data Utilities, and Graphics, GESS Gene Expression Statistical System, 2007, 161-202.*
Agilent, Agilent SurePrint G3 Human Catalog CGH Microarrays, Product Note, 2011, 1-8. (Year: 2011).*
Andre et al., Current Issues in Adjuvant Treatment of Stage II Colon Cancer, Annals of Surgical Oncology, vol. 13, 887-898 (2006).
Benson et al., American Society of Clinical Oncology Recommendations on Adjuvant Chemotherapy for Stage II Colon Cancer, Journal of Clinical Oncology, vol. 22, No. 16, (2004).
Cunninhgam et al., Cetuximab Monotherapy and Cetuximab plus Irinotecan in Irinotecan-Refractory Metastatic Colorectal Cancer, The New England Journal of Medicine, vol. 351, pp. 337-345 (2004).
Dai, Yujia, Platelet-derived growth factor receptor tyrosine kinase inhibitors: a review of the recent patent literature, Expert Opin., Ther. Patents, vol. 20, pp. 885-907 (2010).
Desai et al., SPARC Expression Correlates with Tumor Response to Albumin-Bound Paclitaxel in Head and Neck Cancer Patients, Translational Oncology, vol. 2, No. 2, pp. 59-64 (2009).
Desai et al., Improved effectiveness of nanoparticle albumin-bound (nab) paclitaxel versus polysorbate-based docetaxel in multiple xenografts as a function of HER2 and SPARC status, Anti-Cancer Drugs, vol. 19, pp. 899-909 (2008).
Fearon et al., A Genetic Model for Colorectal Tumorigenesis, Cell., vol. 61, pp. 759-767 (1990).
Gill et al., Pooled Analysis of Fluorouracil-based Adjuvant Therapy for Stage II and III Colon Cancer: Who Benefits and by How Much?, J. Clin. Oncol, vol. 22, pp. 1797-1806 (2004).
Glas et al., Development and Validation of a Robust Prognostic and Predictive Signature for Colorectal Cancer, Journal of Clinical Oncology, vol. 27, No. 15S (2009).
Gotnik et al., Anti-angiogenic tyrosine kinase inhibitors: what is their mechanism of action?, Angiogenesis, vol. 13, pp. 1-14 (2010).
Huang et al., Systematic and integrative analysis of large gene lists using DAVID bioinformatics resources, Nature vol. 4, No. 1, (2009).

(Continued)

Primary Examiner — Amy M Bunker
(74) Attorney, Agent, or Firm — Hoffmann & Baron, LLP

(57) ABSTRACT

The invention relates to methods of typing a sample from a colorectal cancer patient based on the levels of RNA expression products in a cancer cell of the patient. The invention further relates to methods for determining a strategy for treatment of a patient suffering from colorectal cancer, and to methods for assigning treatment to a patient suffering from colorectal cancer.

8 Claims, 13 Drawing Sheets

(56) References Cited

OTHER PUBLICATIONS

Figure 1:
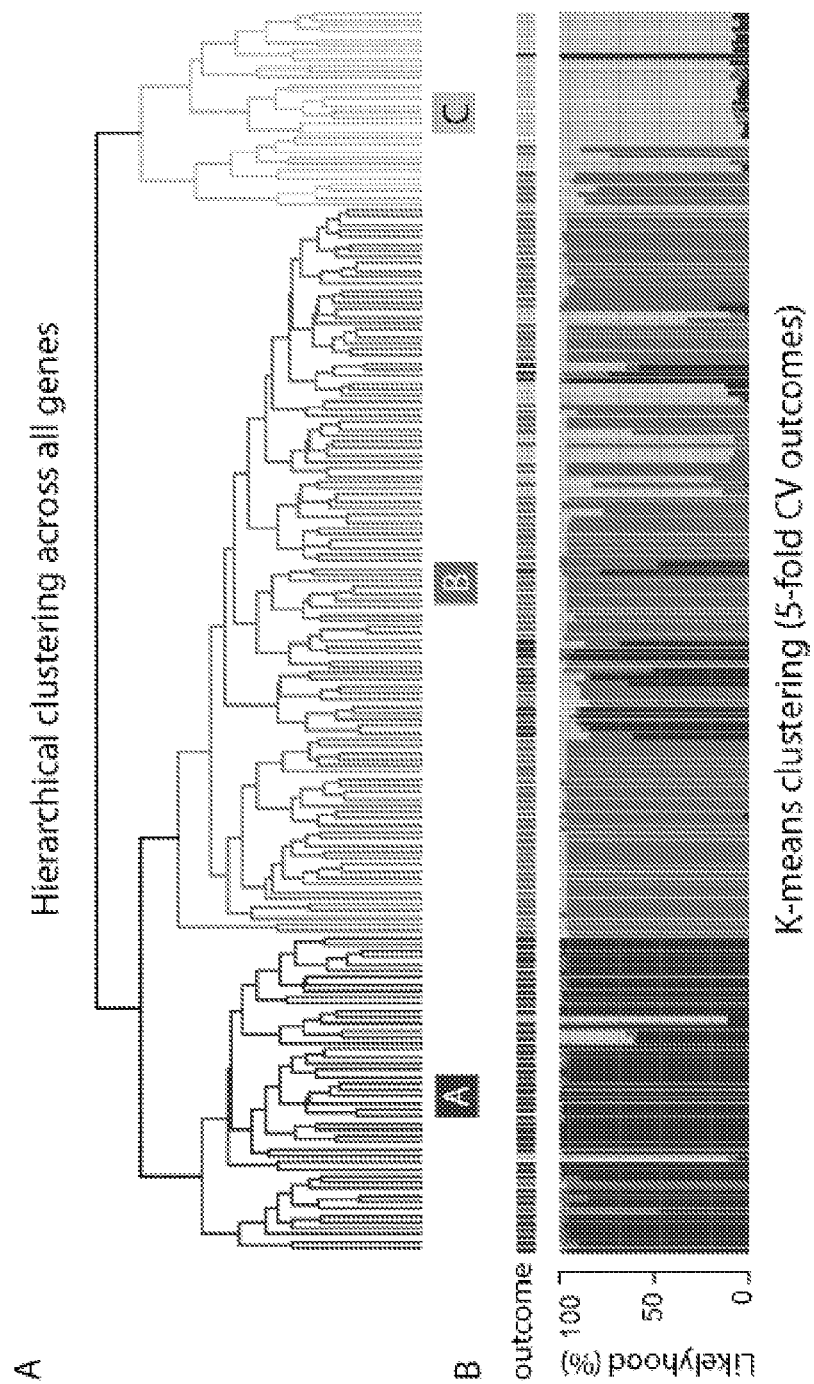

Ionov et al., Ubiquitous somatic mutations in simple repeated sequences reveal a new mechanism for colonic carcinogenesis, Nature, vol. 363, (1993).

Kane et al., Methylation of the hMLH1 Promoter Correlates with Lack of Expression of hMLH1 in Sporadic Colon Tumors and Mismatch Repair-defective Human Tumor Cell Lines, Cancer Res., vol. 57, pp. 808-811 (1997).

Kato-Nakano et al., Characterization and Evaluation of the Antitumour Activity of a Dual-targeting Monoclonal Antibody against Claudin-3 and Claudin-4, Anticancer Research, vol. 30, pp. 4555-4562 (2010).

Kinzler et al., Lessons from Hereditary Colorectal Cancer, Cell, vol. 87, pp. 159-170 (1996).

Lengauer et al., Genetic instabilities in human cancers, Nature, vol. 396, (1998).

Lothe et al., Genomic Instability in Colorectal Cancer: Relationship to Clinicopathological Variables and Family and Family History, Cancer Research, vol. 53, pp. 5849-5852 (1993).

Martin-Magniette et al., Evaluation of the gene-specific dye bias in cDNA microarray experiments, vol. 21, No. 9, pp. 1995-2000 (2005).

Miquel et al., Frequent alteration of DNA damage signalling and repair pathways in human colorectal cancers with microsatellite instability, Oncogene, vol. 26, pp. 5919-5926 (2007).

Murphy et al., Comparison of the Microsatellite Instability Analysis System and the Bethesda Panel for the Determination of Microsatellite Instability in Colorectal Cancers, Journal of Molecular Diagnostics, vol. 8, No. 3, (2006).

Nahta et al., Mechanisms of Disease: understanding resistance to HER2-targeted therapy in human breast cancer, Nature Clinical Practice, vol. 3, No. 5, (2006).

Poynter et al., Molecular Characterization of MSI-H Colorectal Cancer by MLHI Promoter Methylation, Immunohistochemistry, and Mismatch Repair Germline Mutation Screening, Cancer Epidemiol Biomarkers Prev, vol. 17, pp. 3208-3215 (2008).

Pusztai et al., Molecular Classification of Breast Cancer: Limitations and Potential, The Oncologist, vol. 11, pp. 868-877 (2006).

Ribic et al., Tumor Microsatellite-Instability Status as a Predictor of Benefit from Fluorouracil-Based Adjuvant Chemotherapy for Colon Cancer, N. Eng. J. Med., 349:3 (2003).

Ries, US Prevalence Counts, Invasive Cancers only, Jan. 1, 2003 Using Different Tumor Inclusion Criteria, National Cancer Institute, (2003).

Roepman et al., An Immune Reponse Enriched 72-Gene Prognostic Profile for Early-Stage Non-Small-Cell Lung Cancer, Clin. Cancer Res., vol. 15, pp. 284-290 (2009).

Roth et al., Prognostic Role of KRAS and BRAF in Stage II and III Resected Colon Cancer: Results of the Translational Study on the PETACC-3, EORTC 40993, SAKK 60-00 Trial, American Society of Clin. Oncology, (2009).

Shepherd et al., Erlotinib in Previously Treated Non-Small-Cell Lung Cancer, N. Engl. J. Med., vol. 353, No. 2, (2005).

Sobrero, Alberto, Should adjuvant chemotherapy become standard treatment for patients with stage II colon cancer?, Oncology, vol. 7 (2006).

Soreide et al., Microsatellite instability in colorectal cancer, British Journal of Surgery, vol. 93, pp. 395-406 (2006).

Cutsem et al., Open-Label Phase III Trial of Panitumumab Plus Best Supportive Care Compared with Best Supportive Care Alone in Patients with Chemotherapy-Refractory Metastatic Colorectal Cancer, vol. 25, No. 13, pp. 1658-1664 (2007).

Vilar et al., Gene Expression Patterns in Mismatch Repair-Deficient Colorectal Cancers Highlight the Potential Therapeutic Role of Inhibitors of the Phosphatidylinositol 3-Kinase-AKT-Mammalian Target of Rapamycin Pathway, Clin. Cancer Res., vol. 15 (2009).

Warusavitarne et al., The Role of Chemotherapy in Microsatellite Unstable (MSI-H) Colorectal Cancer, Int. J. Colorectal Dis., vol. 22, pp. 739-748 (2007).

Qihan Wu, et al., Molecular cloning and characterization of a novel Dual-specificity Phosphatase18 gene from human fetal brain, Biochimica et Bopphysica Acta 1625 (2003) 296-304.

Jansova E., et al., Comparative transcriptome maps: a new approach to the diagnosis of colorectal carcinoma patients using cDNA microarrays, Clin Genet 2006: 69: 218-227 (XP-002633596.

Kate I. Patterson, et al., Dual-specificity phosphatases: critical regulators with diverse cellular targets, Biochem. J. (2009) 418, 475-489 (XP002673568.

Osellame L D et al., S9.9 MiD51 and MiD49: New mediators of mammalian mitochondrial distribution, Biochimica et Biophysica Acta 1777 (2008) p. 57 XP022758938.

\* cited by examiner

Number of genes

```
                          SEQUENCE LISTING

<160> NUMBER OF SEQ ID NOS: 94

<210> SEQ ID NO 1
<211> LENGTH: 60
<212> TYPE: DNA
<213> ORGANISM: Artificial
<220> FEATURE:
<223> OTHER INFORMATION: Synthetic

<400> SEQUENCE: 1
actaggatat aaactctttg agatagaggt ccatattttt tctttaccta acagcacctg        60

<210> SEQ ID NO 2
<211> LENGTH: 60
<212> TYPE: DNA
<213> ORGANISM: Artificial
<220> FEATURE:
<223> OTHER INFORMATION: Synthetic

<400> SEQUENCE: 2
ctcctttctg tgcacagcac tttattgtta caaagtactc ttccaaaaag ttaccctgtg        60

<210> SEQ ID NO 3
<211> LENGTH: 60
<212> TYPE: DNA
<213> ORGANISM: Artificial
<220> FEATURE:
<223> OTHER INFORMATION: Synthetic

<400> SEQUENCE: 3
tgtgggatgt gttcttcttt ctctgtattc cgatacaaag tgttgtatca aagtgtgata        60

<210> SEQ ID NO 4
<211> LENGTH: 60
<212> TYPE: DNA
<213> ORGANISM: Artificial
<220> FEATURE:
<223> OTHER INFORMATION: Synthetic

<400> SEQUENCE: 4
accagagaaa taataggtat ttgttagacc tgagtgtaca tttcacatgt tatccttcac        60

<210> SEQ ID NO 5
<211> LENGTH: 60
<212> TYPE: DNA
<213> ORGANISM: Artificial
<220> FEATURE:
<223> OTHER INFORMATION: Synthetic

<400> SEQUENCE: 5
gacctcttag gcttggtgtg aggatgaaat gagataggga atataaagca agcagatagt        60

<210> SEQ ID NO 6
<211> LENGTH: 60
<212> TYPE: DNA
<213> ORGANISM: Artificial
<220> FEATURE:
<223> OTHER INFORMATION: Synthetic
```

<400> SEQUENCE: 6
caaggatttc ttatggtggt ttcagtttca tttgcataaa ggtattgaga gggaacaaaa    60

<210> SEQ ID NO 7
<211> LENGTH: 60
<212> TYPE: DNA
<213> ORGANISM: Artificial
<220> FEATURE:
<223> OTHER INFORMATION: Synthetic

<400> SEQUENCE: 7
tatcattcgt cttctttcc aaactacaca tcactgtatg actcaaccag tagcagttat    60

<210> SEQ ID NO 8
<211> LENGTH: 60
<212> TYPE: DNA
<213> ORGANISM: Artificial
<220> FEATURE:
<223> OTHER INFORMATION: Synthetic

<400> SEQUENCE: 8
ttactttctt ggctaaccag tttcttagaa gaaaatgtgt cagggacttg gggatctaca    60

<210> SEQ ID NO 9
<211> LENGTH: 60
<212> TYPE: DNA
<213> ORGANISM: Artificial
<220> FEATURE:
<223> OTHER INFORMATION: Synthetic

<400> SEQUENCE: 9
attcccatcg gcaatgtcta caaggagaaa gccagagtca tcgctgacta ggaggaaaac    60

<210> SEQ ID NO 10
<211> LENGTH: 60
<212> TYPE: DNA
<213> ORGANISM: Artificial
<220> FEATURE:
<223> OTHER INFORMATION: Synthetic

<400> SEQUENCE: 10
ggggtctcat tagctttgca acaggaaaca tcctgtttta ttatggtagt ggggtcagga    60

<210> SEQ ID NO 11
<211> LENGTH: 60
<212> TYPE: DNA
<213> ORGANISM: Artificial
<220> FEATURE:
<223> OTHER INFORMATION: Synthetic

<400> SEQUENCE: 11
agcagagggg atccaacgtc agagctttta gaattacttt tttaagcagc tgtcttctgg    60

<210> SEQ ID NO 12
<211> LENGTH: 60
<212> TYPE: DNA
<213> ORGANISM: Artificial
<220> FEATURE:
<223> OTHER INFORMATION: Synthetic

<400> SEQUENCE: 12
cgaagggctg agctcagatg aggaattcga cagtgtctac gatccctcgt ccattgcatc    60

<210> SEQ ID NO 13
<211> LENGTH: 60

```
<212> TYPE: DNA
<213> ORGANISM: Artificial
<220> FEATURE:
<223> OTHER INFORMATION: Synthetic

<400> SEQUENCE: 13
caaggttcta ttaaccactt ctaagggtac acctccctcc aaactactgc attttctatg    60

<210> SEQ ID NO 14
<211> LENGTH: 60
<212> TYPE: DNA
<213> ORGANISM: Artificial
<220> FEATURE:
<223> OTHER INFORMATION: Synthetic

<400> SEQUENCE: 14
gtttgcacag ttctagacac gataaataca tgtgaaatca cacaactcag aaaatgtccc    60

<210> SEQ ID NO 15
<211> LENGTH: 60
<212> TYPE: DNA
<213> ORGANISM: Artificial
<220> FEATURE:
<223> OTHER INFORMATION: Synthetic

<400> SEQUENCE: 15
ctgtctccag gtaggtggac cagagaactt gagcgaagct caagccttct caactcaagg    60

<210> SEQ ID NO 16
<211> LENGTH: 60
<212> TYPE: DNA
<213> ORGANISM: Artificial
<220> FEATURE:
<223> OTHER INFORMATION: Synthetic

<400> SEQUENCE: 16
gtttttgatg gccttttaaa caagactcca gtatgtgaag gttaattgct gtgctccaca    60

<210> SEQ ID NO 17
<211> LENGTH: 60
<212> TYPE: DNA
<213> ORGANISM: Artificial
<220> FEATURE:
<223> OTHER INFORMATION: Synthetic

<400> SEQUENCE: 17
agtaagcata ctgaagtgag ttcgggtact gagtgcagga taaagctatt cttatccttt    60

<210> SEQ ID NO 18
<211> LENGTH: 60
<212> TYPE: DNA
<213> ORGANISM: Artificial
<220> FEATURE:
<223> OTHER INFORMATION: Synthetic

<400> SEQUENCE: 18
ggcagaatta cagctgagcg gggacaacaa agagttcttc tctgggaaaa gttttgtctt    60

<210> SEQ ID NO 19
<211> LENGTH: 60
<212> TYPE: DNA
<213> ORGANISM: Artificial
<220> FEATURE:
<223> OTHER INFORMATION: Synthetic

<400> SEQUENCE: 19
```
tgtcattctg aaaacatcct atgcgatgga atggagaagg aagtgatgac tcagagtgtg    60

<210> SEQ ID NO 20
<211> LENGTH: 60
<212> TYPE: DNA
<213> ORGANISM: Artificial
<220> FEATURE:
<223> OTHER INFORMATION: Synthetic

<400> SEQUENCE: 20
ttgaagttgg aaatccaagg ggaatctaaa accgaccaga tgtttctgct gctggaaagg    60

<210> SEQ ID NO 21
<211> LENGTH: 60
<212> TYPE: DNA
<213> ORGANISM: Artificial
<220> FEATURE:
<223> OTHER INFORMATION: Synthetic

<400> SEQUENCE: 21
attggcttcg agtggttgca tctgacaagg agacctacga acttcgttac ttccagatta    60

<210> SEQ ID NO 22
<211> LENGTH: 60
<212> TYPE: DNA
<213> ORGANISM: Artificial
<220> FEATURE:
<223> OTHER INFORMATION: Synthetic

<400> SEQUENCE: 22
tgggcattgc agtaggtacc agtgagaaaa aagggaaaa tctgcatatt gagtatttat    60

<210> SEQ ID NO 23
<211> LENGTH: 60
<212> TYPE: DNA
<213> ORGANISM: Artificial
<220> FEATURE:
<223> OTHER INFORMATION: Synthetic

<400> SEQUENCE: 23
agtcaaagaa gcaggggaaa agtaagctcc tccaaagttg cttgcagtgc tggaaataga    60

<210> SEQ ID NO 24
<211> LENGTH: 60
<212> TYPE: DNA
<213> ORGANISM: Artificial
<220> FEATURE:
<223> OTHER INFORMATION: Synthetic

<400> SEQUENCE: 24
ttcctggaga gggagaaatg cgtggatacc ttagacttct ggtttgcctg caatggattc    60

<210> SEQ ID NO 25
<211> LENGTH: 60
<212> TYPE: DNA
<213> ORGANISM: Artificial
<220> FEATURE:
<223> OTHER INFORMATION: Synthetic

<400> SEQUENCE: 25
gacttcgacg agttcctgaa gatgatggag gacgtgcagt aaggagtgga cagtcgcctc    60

<210> SEQ ID NO 26
<211> LENGTH: 60
<212> TYPE: DNA
<213> ORGANISM: Artificial

```
<220> FEATURE:
<223> OTHER INFORMATION: Synthetic

<400> SEQUENCE: 26
attggctggt caggatatac aaggtaaagg acctggataa tcgaggcttg tcaaggacat    60

<210> SEQ ID NO 27
<211> LENGTH: 60
<212> TYPE: DNA
<213> ORGANISM: Artificial
<220> FEATURE:
<223> OTHER INFORMATION: Synthetic

<400> SEQUENCE: 27
agagacactg ggctggccta gacactgcct ttggtgatac cctaaaccaa aggggccagt    60

<210> SEQ ID NO 28
<211> LENGTH: 60
<212> TYPE: DNA
<213> ORGANISM: Artificial
<220> FEATURE:
<223> OTHER INFORMATION: Synthetic

<400> SEQUENCE: 28
catatacttt gtcttgcctg tatgcagccc ttgtgtaata tggtgaatta gagtggtatt    60

<210> SEQ ID NO 29
<211> LENGTH: 60
<212> TYPE: DNA
<213> ORGANISM: Artificial
<220> FEATURE:
<223> OTHER INFORMATION: Synthetic

<400> SEQUENCE: 29
gagtggtaag attttattgt gtcaaacgac tgcattagtt gtgttttgtt attatggcag    60

<210> SEQ ID NO 30
<211> LENGTH: 60
<212> TYPE: DNA
<213> ORGANISM: Artificial
<220> FEATURE:
<223> OTHER INFORMATION: Synthetic

<400> SEQUENCE: 30
ttaacaagga gctagccaaa cttctctgag agtttgagga ggtagcctga gaggatcatt    60

<210> SEQ ID NO 31
<211> LENGTH: 60
<212> TYPE: DNA
<213> ORGANISM: Artificial
<220> FEATURE:
<223> OTHER INFORMATION: Synthetic

<400> SEQUENCE: 31
gtggaggaca cttcaatcta aagtgatctt aaaggaggag tagtaggatt tgaagatgaa    60

<210> SEQ ID NO 32
<211> LENGTH: 60
<212> TYPE: DNA
<213> ORGANISM: Artificial
<220> FEATURE:
<223> OTHER INFORMATION: Synthetic

<400> SEQUENCE: 32
gttattcgta ttcaacaagt ggaatttta ctttgctgtt ctcagaaacc catgaatctg    60
```

<210> SEQ ID NO 33
<211> LENGTH: 60
<212> TYPE: DNA
<213> ORGANISM: Artificial
<220> FEATURE:
<223> OTHER INFORMATION: Synthetic

<400> SEQUENCE: 33
ggacttcctt gcttttctct acttccaaat cacaatttct tacaaccaag ctttgtgctc    60

<210> SEQ ID NO 34
<211> LENGTH: 60
<212> TYPE: DNA
<213> ORGANISM: Artificial
<220> FEATURE:
<223> OTHER INFORMATION: Synthetic

<400> SEQUENCE: 34
caacttgaat ttgatcccat aaagtcaggc atcaggaagc cattcagaat ttttcaccct    60

<210> SEQ ID NO 35
<211> LENGTH: 60
<212> TYPE: DNA
<213> ORGANISM: Artificial
<220> FEATURE:
<223> OTHER INFORMATION: Synthetic

<400> SEQUENCE: 35
tgtgatgaca cacatatgat ctttcgtgtt tctgagcgac tctactttca ttgtttgcca    60

<210> SEQ ID NO 36
<211> LENGTH: 60
<212> TYPE: DNA
<213> ORGANISM: Artificial
<220> FEATURE:
<223> OTHER INFORMATION: Synthetic

<400> SEQUENCE: 36
gttcacaaaa acacctagta ggtattcagt tcatattgga atgaatgaga aaatgagcag    60

<210> SEQ ID NO 37
<211> LENGTH: 60
<212> TYPE: DNA
<213> ORGANISM: Artificial
<220> FEATURE:
<223> OTHER INFORMATION: Synthetic

<400> SEQUENCE: 37
aagaactttg gaagagatca gctggaaata tatctcattt attttatgaa taaatatgaa    60

<210> SEQ ID NO 38
<211> LENGTH: 60
<212> TYPE: DNA
<213> ORGANISM: Artificial
<220> FEATURE:
<223> OTHER INFORMATION: Synthetic

<400> SEQUENCE: 38
cctgtcttga ctgctgacgt tcctcaatga ttctattgtc tattttatgg gaagcagcct    60

<210> SEQ ID NO 39
<211> LENGTH: 60
<212> TYPE: DNA
<213> ORGANISM: Artificial
<220> FEATURE:
<223> OTHER INFORMATION: Synthetic

<400> SEQUENCE: 39
ggcaaatgta aactcagcct ttcattcatg acgtgtgaaa tttcagtttc tctggagttt    60

<210> SEQ ID NO 40
<211> LENGTH: 60
<212> TYPE: DNA
<213> ORGANISM: Artificial
<220> FEATURE:
<223> OTHER INFORMATION: Synthetic

<400> SEQUENCE: 40
acaatgacgt gcttcgacaa caggtggaag atcttaaaaa caagaatctg ctgcttcgag    60

<210> SEQ ID NO 41
<211> LENGTH: 60
<212> TYPE: DNA
<213> ORGANISM: Artificial
<220> FEATURE:
<223> OTHER INFORMATION: Synthetic

<400> SEQUENCE: 41
gtgtgaaatt tcagtttctc tggagtttgt cagacggcgt gggaaccacg cctgaaactc    60

<210> SEQ ID NO 42
<211> LENGTH: 60
<212> TYPE: DNA
<213> ORGANISM: Artificial
<220> FEATURE:
<223> OTHER INFORMATION: Synthetic

<400> SEQUENCE: 42
caacttgaat ttgatcccat aaagtcaggc atcaggaagc cattcagaat ttttcaccct    60

<210> SEQ ID NO 43
<211> LENGTH: 60
<212> TYPE: DNA
<213> ORGANISM: Artificial
<220> FEATURE:
<223> OTHER INFORMATION: Synthetic

<400> SEQUENCE: 43
ttgccaaccc tggtatgctg gagcaatgga aagattgcaa gcagagaccg aacttattaa    60

<210> SEQ ID NO 44
<211> LENGTH: 60
<212> TYPE: DNA
<213> ORGANISM: Artificial
<220> FEATURE:
<223> OTHER INFORMATION: Synthetic

<400> SEQUENCE: 44
tgccaggttt aaccactcat agcaacaaga cttttaccca gagaccaaaa cctatagacc    60

<210> SEQ ID NO 45
<211> LENGTH: 60
<212> TYPE: DNA
<213> ORGANISM: Artificial
<220> FEATURE:
<223> OTHER INFORMATION: Synthetic

<400> SEQUENCE: 45
agcaaaaaag tcgaactttt tctgttgaac aaaatattca caacagggca gttgtgatac    60

<210> SEQ ID NO 46

```
<211> LENGTH: 60
<212> TYPE: DNA
<213> ORGANISM: Artificial
<220> FEATURE:
<223> OTHER INFORMATION: Synthetic

<400> SEQUENCE: 46
ctgctggagg gacactgctg gcaaacggag acctatttt gtacaaagaa cccttgacct     60

<210> SEQ ID NO 47
<211> LENGTH: 60
<212> TYPE: DNA
<213> ORGANISM: Artificial
<220> FEATURE:
<223> OTHER INFORMATION: Synthetic

<400> SEQUENCE: 47
ctgtcagggc tgacttcacc tctgctcatc tcagtttcct aatctgtaaa atgggtctaa    60

<210> SEQ ID NO 48
<211> LENGTH: 60
<212> TYPE: DNA
<213> ORGANISM: Artificial
<220> FEATURE:
<223> OTHER INFORMATION: Synthetic

<400> SEQUENCE: 48
gtggtcattt tgatgatatg tgtgtaaaat gtgaataatc caattggtgt ctgtactcag    60

<210> SEQ ID NO 49
<211> LENGTH: 60
<212> TYPE: DNA
<213> ORGANISM: Artificial
<220> FEATURE:
<223> OTHER INFORMATION: Synthetic

<400> SEQUENCE: 49
agagaaaagt acaagacaga aatcttctag cactttgtaa acacagtgaa taacctcttg    60

<210> SEQ ID NO 50
<211> LENGTH: 60
<212> TYPE: DNA
<213> ORGANISM: Artificial
<220> FEATURE:
<223> OTHER INFORMATION: Synthetic

<400> SEQUENCE: 50
atattcctca gactcaacaa ttcttgttct ttagaactgt gttctcacct tcccaacact    60

<210> SEQ ID NO 51
<211> LENGTH: 60
<212> TYPE: DNA
<213> ORGANISM: Artificial
<220> FEATURE:
<223> OTHER INFORMATION: Synthetic

<400> SEQUENCE: 51
gtgcaatttg gcagacaagt tggtgaaagg taagttgtct ccagagattt caatcaggga    60

<210> SEQ ID NO 52
<211> LENGTH: 60
<212> TYPE: DNA
<213> ORGANISM: Artificial
<220> FEATURE:
<223> OTHER INFORMATION: Synthetic

<400> SEQUENCE: 52
```
tcagctttgg aactcctcag ccctgagttt ggtctttagt cgcctctgag aactttaatt    60

<210> SEQ ID NO 53
<211> LENGTH: 60
<212> TYPE: DNA
<213> ORGANISM: Artificial
<220> FEATURE:
<223> OTHER INFORMATION: Synthetic

<400> SEQUENCE: 53
ctcctaatta ggtgcctagg aagagtccca tctgagcagg aagacatttc tctttccttt    60

<210> SEQ ID NO 54
<211> LENGTH: 60
<212> TYPE: DNA
<213> ORGANISM: Artificial
<220> FEATURE:
<223> OTHER INFORMATION: Synthetic

<400> SEQUENCE: 54
aaagaagata tcgaataact tggaaaaatg ggtacttagt gcggtggcaa aagccaaaca    60

<210> SEQ ID NO 55
<211> LENGTH: 60
<212> TYPE: DNA
<213> ORGANISM: Artificial
<220> FEATURE:
<223> OTHER INFORMATION: Synthetic

<400> SEQUENCE: 55
tttttgaatc tttcgtagcc taaaagacaa ttttccttgg aacacataag aactgtgcag    60

<210> SEQ ID NO 56
<211> LENGTH: 60
<212> TYPE: DNA
<213> ORGANISM: Artificial
<220> FEATURE:
<223> OTHER INFORMATION: Synthetic

<400> SEQUENCE: 56
tttcctactg cagccttcag attctcatca ttttgcatct attttgtagc caataaaact    60

<210> SEQ ID NO 57
<211> LENGTH: 60
<212> TYPE: DNA
<213> ORGANISM: Artificial
<220> FEATURE:
<223> OTHER INFORMATION: Synthetic

<400> SEQUENCE: 57
tgttaaacta caaaactgta cagcctattt tagtgtggac tattaaaacc cttgcactgt    60

<210> SEQ ID NO 58
<211> LENGTH: 60
<212> TYPE: DNA
<213> ORGANISM: Artificial
<220> FEATURE:
<223> OTHER INFORMATION: Synthetic

<400> SEQUENCE: 58
tctagatgct tctactgtta tgttttatct gcccatttat ctttcttagt taccaggaga    60

<210> SEQ ID NO 59
<211> LENGTH: 60
<212> TYPE: DNA

<213> ORGANISM: Artificial
<220> FEATURE:
<223> OTHER INFORMATION: Synthetic

<400> SEQUENCE: 59
tatataaata cacagagttt ggtatgatat ttaaatacat catctggcca ggcatggtgg    60

<210> SEQ ID NO 60
<211> LENGTH: 60
<212> TYPE: DNA
<213> ORGANISM: Artificial
<220> FEATURE:
<223> OTHER INFORMATION: Synthetic

<400> SEQUENCE: 60
ttgttttgca aaggcccaag tcctcctgct aggaaaagct tttgcatgtg tcctgaatgt    60

<210> SEQ ID NO 61
<211> LENGTH: 60
<212> TYPE: DNA
<213> ORGANISM: Artificial
<220> FEATURE:
<223> OTHER INFORMATION: Synthetic

<400> SEQUENCE: 61
tgtgagagtt taaagtgggc aggacatact agggtttagc attttagcca atgtcttcct    60

<210> SEQ ID NO 62
<211> LENGTH: 60
<212> TYPE: DNA
<213> ORGANISM: Artificial
<220> FEATURE:
<223> OTHER INFORMATION: Synthetic

<400> SEQUENCE: 62
tgtgtcaagg aaagggcttt atttgtgaat tttgccagaa tacgactgtc atcttcccat    60

<210> SEQ ID NO 63
<211> LENGTH: 60
<212> TYPE: DNA
<213> ORGANISM: Artificial
<220> FEATURE:
<223> OTHER INFORMATION: Synthetic

<400> SEQUENCE: 63
aaacaaatag aagagctttta ctcaatctcc atgtgaagtt caaggaaagt tcttctcagt    60

<210> SEQ ID NO 64
<211> LENGTH: 60
<212> TYPE: DNA
<213> ORGANISM: Artificial
<220> FEATURE:
<223> OTHER INFORMATION: Synthetic

<400> SEQUENCE: 64
tccgagcgta agaagcctct ggacattgac tacatggggg aggaacagct ccgggagaaa    60

<210> SEQ ID NO 65
<211> LENGTH: 60
<212> TYPE: DNA
<213> ORGANISM: Artificial
<220> FEATURE:
<223> OTHER INFORMATION: Synthetic

<400> SEQUENCE: 65
ctggagtcta ctatgtcttc tttcaactag agctgcggcg cgtggtggcc ggcgagggct    60

<210> SEQ ID NO 66
<211> LENGTH: 60
<212> TYPE: DNA
<213> ORGANISM: Artificial
<220> FEATURE:
<223> OTHER INFORMATION: Synthetic

<400> SEQUENCE: 66
cgtaacatac cagttagggc ctgcggaagc atcttgtaat ggaacacatt actatttctg    60

<210> SEQ ID NO 67
<211> LENGTH: 60
<212> TYPE: DNA
<213> ORGANISM: Artificial
<220> FEATURE:
<223> OTHER INFORMATION: Synthetic

<400> SEQUENCE: 67
ctcctcaatc tggtttatga acaactgac aaacaccttt ctcctgatgg ccagtatgtc     60

<210> SEQ ID NO 68
<211> LENGTH: 60
<212> TYPE: DNA
<213> ORGANISM: Artificial
<220> FEATURE:
<223> OTHER INFORMATION: Synthetic

<400> SEQUENCE: 68
ccatcgctgt ttgacataac ctcctgattc tattattgtc acagcattaa cctccacagt    60

<210> SEQ ID NO 69
<211> LENGTH: 60
<212> TYPE: DNA
<213> ORGANISM: Artificial
<220> FEATURE:
<223> OTHER INFORMATION: Synthetic

<400> SEQUENCE: 69
tgtggtacct ttgtacatgt ttgattctgt attctttatt ccagtgtggc atatgtgccc    60

<210> SEQ ID NO 70
<211> LENGTH: 60
<212> TYPE: DNA
<213> ORGANISM: Artificial
<220> FEATURE:
<223> OTHER INFORMATION: Synthetic

<400> SEQUENCE: 70
tgccttcatc tcagatttgt tcatcacagg tggatcccat gtgtcttcag tagacaagtc    60

<210> SEQ ID NO 71
<211> LENGTH: 60
<212> TYPE: DNA
<213> ORGANISM: Artificial
<220> FEATURE:
<223> OTHER INFORMATION: Synthetic

<400> SEQUENCE: 71
acgttgcatt gttgtggtgt caccgattat agagattgga cagatactaa ttattactca    60

<210> SEQ ID NO 72
<211> LENGTH: 60
<212> TYPE: DNA
<213> ORGANISM: Artificial
<220> FEATURE:

<223> OTHER INFORMATION: Synthetic

<400> SEQUENCE: 72
ttagtgttgc atctgatttt caggtgtaca tttattttg actgggcaga tagggattt    60

<210> SEQ ID NO 73
<211> LENGTH: 60
<212> TYPE: DNA
<213> ORGANISM: Artificial
<220> FEATURE:
<223> OTHER INFORMATION: Synthetic

<400> SEQUENCE: 73
gctttaaaaa ggatggattt caaatacact gtgcccacta gaagcttcga agggcctcgt    60

<210> SEQ ID NO 74
<211> LENGTH: 60
<212> TYPE: DNA
<213> ORGANISM: Artificial
<220> FEATURE:
<223> OTHER INFORMATION: Synthetic

<400> SEQUENCE: 74
aaagtcagat cttgtgaatg aagaagcaac tggacagttc catgtatacc aagaaaatgc    60

<210> SEQ ID NO 75
<211> LENGTH: 60
<212> TYPE: DNA
<213> ORGANISM: Artificial
<220> FEATURE:
<223> OTHER INFORMATION: Synthetic

<400> SEQUENCE: 75
acactgaagc gactgcagag ccagaaggga gtgcagggaa tcatcgtcgt gaacacagaa    60

<210> SEQ ID NO 76
<211> LENGTH: 60
<212> TYPE: DNA
<213> ORGANISM: Artificial
<220> FEATURE:
<223> OTHER INFORMATION: Synthetic

<400> SEQUENCE: 76
atgatgaaca gagttatgat tcctatgata acagctatag caccccagcc caaagtggtg    60

<210> SEQ ID NO 77
<211> LENGTH: 60
<212> TYPE: DNA
<213> ORGANISM: Artificial
<220> FEATURE:
<223> OTHER INFORMATION: Synthetic

<400> SEQUENCE: 77
caaactccat ccagtacatt ctttcttctt tcatgaaaga gcttgagttg gatgtaaata    60

<210> SEQ ID NO 78
<211> LENGTH: 60
<212> TYPE: DNA
<213> ORGANISM: Artificial
<220> FEATURE:
<223> OTHER INFORMATION: Synthetic

<400> SEQUENCE: 78
cagctgccca tgagcattcg gatcaacagc caagcctccg aaagccgcca ggactctgct    60

```
<210> SEQ ID NO 79
<211> LENGTH: 60
<212> TYPE: DNA
<213> ORGANISM: Artificial
<220> FEATURE:
<223> OTHER INFORMATION: Synthetic

<400> SEQUENCE: 79
ggggtttagg gtcgagctgt tcctgatgtt tatcggagac tgggatcaaa gctatccagg    60

<210> SEQ ID NO 80
<211> LENGTH: 60
<212> TYPE: DNA
<213> ORGANISM: Artificial
<220> FEATURE:
<223> OTHER INFORMATION: Synthetic

<400> SEQUENCE: 80
cagctgaata ccacagacaa ggagagcacc tattttaaa cctaaatgag gtataaggac    60

<210> SEQ ID NO 81
<211> LENGTH: 60
<212> TYPE: DNA
<213> ORGANISM: Artificial
<220> FEATURE:
<223> OTHER INFORMATION: Synthetic

<400> SEQUENCE: 81
aatagggttg tctttcctat gaaaatgcca tctgtagacc ttgtgagtca gccgtccaga    60

<210> SEQ ID NO 82
<211> LENGTH: 60
<212> TYPE: DNA
<213> ORGANISM: Artificial
<220> FEATURE:
<223> OTHER INFORMATION: Synthetic

<400> SEQUENCE: 82
aaagagcctg ggtgtttggg tcagataaat gaagatcaaa ctccagctcc agcctcattt    60

<210> SEQ ID NO 83
<211> LENGTH: 60
<212> TYPE: DNA
<213> ORGANISM: Artificial
<220> FEATURE:
<223> OTHER INFORMATION: Synthetic

<400> SEQUENCE: 83
tttttctttt tgaagagttt taagaagttg taactttttg tgtcttgtca tgtcagagaa    60

<210> SEQ ID NO 84
<211> LENGTH: 60
<212> TYPE: DNA
<213> ORGANISM: Artificial
<220> FEATURE:
<223> OTHER INFORMATION: Synthetic

<400> SEQUENCE: 84
aagcgaatga taagggaaaa gttctcaggg aattgaagtg ttgttgctat ggtgacgtcc    60

<210> SEQ ID NO 85
<211> LENGTH: 60
<212> TYPE: DNA
<213> ORGANISM: Artificial
<220> FEATURE:
<223> OTHER INFORMATION: Synthetic
```

<400> SEQUENCE: 85
aagatctcag ggtagggaaa aaccagtgaa tgaggttaca cagcaggaaa agaaccggtt    60

<210> SEQ ID NO 86
<211> LENGTH: 60
<212> TYPE: DNA
<213> ORGANISM: Artificial
<220> FEATURE:
<223> OTHER INFORMATION: Synthetic

<400> SEQUENCE: 86
ctgtactgga tgtgaactga gcgtatatct gtttttaggt gtctttaagc caatgtggag    60

<210> SEQ ID NO 87
<211> LENGTH: 60
<212> TYPE: DNA
<213> ORGANISM: Artificial
<220> FEATURE:
<223> OTHER INFORMATION: Synthetic

<400> SEQUENCE: 87
agttctcttt atcgccaaaa tcacgccaaa taataacggg acctatgcct gttttgtctc    60

<210> SEQ ID NO 88
<211> LENGTH: 60
<212> TYPE: DNA
<213> ORGANISM: Artificial
<220> FEATURE:
<223> OTHER INFORMATION: Synthetic

<400> SEQUENCE: 88
aaacagcact tgaggtctca tcaattaaag caccttgtgg aatctgtttc ctatatttga    60

<210> SEQ ID NO 89
<211> LENGTH: 60
<212> TYPE: DNA
<213> ORGANISM: Artificial
<220> FEATURE:
<223> OTHER INFORMATION: Synthetic

<400> SEQUENCE: 89
gacatctcgc tgtaatgcag tgggagaagt aaaagattat gagcctccat ttggttccaa    60

<210> SEQ ID NO 90
<211> LENGTH: 60
<212> TYPE: DNA
<213> ORGANISM: Artificial
<220> FEATURE:
<223> OTHER INFORMATION: Synthetic

<400> SEQUENCE: 90
aacagttaac aggatgcaga catggcagag gtttcctaaa aatctcatta tctataacca    60

<210> SEQ ID NO 91
<211> LENGTH: 60
<212> TYPE: DNA
<213> ORGANISM: Artificial
<220> FEATURE:
<223> OTHER INFORMATION: Synthetic

<400> SEQUENCE: 91
ctcatggcgg aattagaaga actagaacag gaggaaccag acaagaattt gctggaagtc    60

<210> SEQ ID NO 92
<211> LENGTH: 60

```
<212> TYPE: DNA
<213> ORGANISM: Artificial
<220> FEATURE:
<223> OTHER INFORMATION: Synthetic

<400> SEQUENCE: 92
gatggtgggc taaattttaa ttctcaaaag tgtaggaggc taatattgtc ttctaagttc    60

<210> SEQ ID NO 93
<211> LENGTH: 60
<212> TYPE: DNA
<213> ORGANISM: Artificial
<220> FEATURE:
<223> OTHER INFORMATION: Synthetic

<400> SEQUENCE: 93
cccagaaaac ctccagtagt ggacaacagg ttttcaccat agcctacgtt aacccatttt    60

<210> SEQ ID NO 94
<211> LENGTH: 60
<212> TYPE: DNA
<213> ORGANISM: Artificial
<220> FEATURE:
<223> OTHER INFORMATION: Synthetic

<400> SEQUENCE: 94
cagcaaatgt actaatttac actgtcactg tatacttctc cctataacct tgtaagtgtt    60
```

METHODS AND MEANS FOR MOLECULAR CLASSIFICATION OF COLORECTAL CANCERS

This application is the U.S. National Phase of, and Applicants claim priority from, International Application No. PCT/NL2011/050901 filed Dec. 23, 2011, which claims priority from European Application No. EP 10196768.5 filed Dec. 23, 2010, each of which are incorporated herein by reference.

FIELD

The invention relates to the field of oncology. More specifically, the invention relates to a method for typing colorectal cancer cells. The invention provides means and methods for molecular classification of colorectal cancer cells.

Worldwide over a million new cases of colorectal cancer (CRC) were diagnosed in 2002, accounting for more than 9% of all new cancer cases [Ries et al. SEER Cancer Statistics Review, 1975-2003. Bethesda, Md.: National Cancer Institute, 2006]. CRC is the third most common cancer worldwide after lung and breast with two-thirds of all colorectal cancers occurring in the more developed regions. As with all cancers, chances of survival are good for patients when the cancer is detected in an early stage. Stage I patients have a survival rate of ~93% while the 5-year survival rate drops to ~80% in stage II patients and to 60% in stage III patients [Sobrero et al, 2006. Lancet Oncol 7: 515-6]. Despite numerous clinical trials, the benefit of adjuvant chemotherapy for stage II colon cancer patients is still debatable [Andre et al, 2006. Ann Surg Oncol 13: 887-98]. Several analyses and meta-analyses have been performed of clinical trials comparing adjuvant therapy with observation in patients with stage II colon or colorectal cancer [reviewed in Benson et al, 2004. J Clin Oncol 15: 3408-19]. Three-fourth of patients is cured by surgery alone and therefore, less than 25% of patients would benefit from additional chemotherapy. For stage III patients, adjuvant treatment is recommended for all patients [Gill et al, 2004. J Clin Oncol 22:1797-806] although patients with T1 or T2 N1 M0 tumors (stage III A) have a significantly better survival rate than stage II B patients indicating that many patients would not require additional chemotherapy.

The identification of the sub-group of patients who are more likely to suffer from a recurrent disease and who are more likely to benefit from adjuvant treatment after surgery would allow a more personalized treatment approach for the heterogeneous CRC patient population. Much effort has been put on the identification of clinico-pathological parameters that predict prognosis and therapy response. Although some clinical parameters have been shown to correlate with outcome, physicians acknowledge that the present parameters are insufficient to correctly classify colon cancer patients. The identification of better risk factors and classification methods is therefore required.

Besides adjuvant chemotherapy, new targeted therapies, such as monoclonal antibody inhibitors, are in development that target specific proteins and receptors of the cancer cells. The identification of the ErbB receptor family as oncogenes has led to the development of various targeted anticancer therapeutics including gefitinib and erlotinib for lung cancer [Shepherd et al, 2005. N Engl J Med 353: 123-32], and lapatinib and Herceptin for breast cancer [Nahta et al, 2006. Nat Clin Pract Oncol 3: 269-80]. Many therapeutic approaches are aimed directly at the Epidermal Growth Factor Receptor (EGFR, also known as ErbB-1 or HER1) with Cetuximab (Erbitux) [Cunningham et al, 2004. N Engl J Med 351: 337-45.], and Panitumumab [Van Cutsem et al, 2007. J Clin Oncol 25: 1658-64] as examples of monoclonal antibody inhibitors in colon cancer. As many of these targeted therapies will be enormously cost-intensive it becomes more important to identify patients who will benefit from these drugs, or to eliminate patients who will certainly not profit from them.

More than 70% of colon cancers are sporadic without any inherited genetic risk factor. Traditionally, a progressive model has been proposed to explain the development of colon cancer [Fearon and Vogelstein 1990. Cell 61: 759-67; Kinzler and Vogelstein 1996. Cell 87: 159-70.]. This model involves stepwise accumulation of genetic alterations into several key oncogenes and tumor suppressor genes such as KRAS, BRAF, TP53 and importantly the adenomatous polyposis coli (APC) gene which accounts for approximately 80% of all CRC and is mutated in the germline of patients with Familial adenomatous polyposis (FAP). However, increased knowledge of progression from adenoma to carcinoma and more detailed molecular analyses of colon cancer have revealed that CRC is more heterogeneous with regard to genetic and molecular alterations. The majority of sporadic colon cancers are thought to be caused by defects in key genes and genetic loci, including cell cycle check points and telomere functions, that result in aneuploid and polyploid karyotypes and various structural chromosomal aberrations [Lengauer et al, 1998. Nature 396: 643-9]. These tumors display a chromosomal instability (CIN) phenotype and account of approximately 85% of all sporadic colon cancers.

A second class of colon tumors manifests a microsatellite instability (MSI) phenotype in which chromosome losses or gains are rarer [Lothe et al, 1993. Cancer Res 53: 5849-52]. These tumors typically display various insertions or deletions, most common in short tandem repeats, the so-called microsatellites [Ionov et al, 1993. Nature 363: 558-61]. MSI occurs in 10-20% of colon tumors and has been attributed predominantly to gene silencing of DNA mismatch repairs (MMR) genes by mutation or methylation, including MSH2, PMS2 and in particular MLH1 [Kane et al, 1997. Cancer Res 57: 808-11]. Consequently, the MSI phenotype is also referred to as the MMR deficient (dMMR) phenotype. Three different categories have been determined based on the MSI status: MSI-High (MSI-H), unstable for 30% of the used markers; MSI-Low (MSI-L), unstable for 10-30% of markers; and microsatillite stable (MSS) that do not display MSI. Molecular characterization of patients with MSI-H tumors indicated that 91% had at least one MMR gene (hyper) methylated and 54% showed MLH1 (hyper)methylation [Poynter et al, 2008. Cancer Epidemiol Biomarkers Prev 17: 3208-15]. Clinical studies have demonstrated that MSI rates vary with tumor stage, and in the adjuvant setting, MSI-H have been associated with longer survival than patients with MSS tumors [Roth et al, 2009. J Clin Oncol 27: 169s]. Although MSI tumors show a stable karyotype, the deficiencies in MMR genes leads to loss of function of tumor suppressor genes and is associated with activating mutations in oncogenes such as BRAF [Miguel et al, 2007. Oncogene 26: 5919-26].

The molecular background of patients plays an important role in their response to treatment. Patients with MSI-H cancers seem to have different behaviour patterns and responses to chemotherapy compared with MSS patients [Warusavitarne and Schnitzler et al, 2007. Int J Colorectal Dis 22: 739-48]. As mentioned above, the mutation or hypermethylation of the mismatch repair system causes the MSI-H status. The MMR involves the recognition and repair of incorrectly paired nucleotides during DNA replication. 5-Fluoro-uracil based chemotherapy (5FU) is the standard treatment for stage 3 colorectal cancer after surgery, and the survival advantage associated with this treatment is about 10-20%. The response is increased by combining 5FU with other chemotherapeutic agents such as irinotecan and oxiplatin. 5FU acts through the inhibition of thymidylate synthase and the incorporation of fraudulent bases into DNA and RNA. Patients with MSI-H and in-vitro data on cell lines with defective MMR indicate that MSI-H leads to resistance to 5FU treatment [Warusavitarne and Schnitzler et al, 2007. Int J Colorectal Dis 22: 739-48]. The most likely mechanism by which 5FU resistance is conferred are possible reduced thymidylate synthase activity and inability of MMR genes to bind 5FU-modified DNA.

Although clinical data are still somewhat conflicting, the analysis of 570 patients with stage II and III colorectal cancer from pooled randomized controlled trials indicate that MSI-H had no benefit from the 5-FU treatment [Ribic et al, 2003. N Engl J Med 349: 247-57]. While in the no-treatment group patients with MSI-H tumours had a better 5-year survival rate, there was no increase in 5-year survival in the MSI-H group that received 5-FU based chemotherapy. In fact, the study went on to show a trend to reduced survival in patients with MSI-H receiving 5FU chemotherapy; this most likely results from the toxicity of chemotherapy. Other studies have shown that MSI-H colorectal cancer is specifically sensitive to compounds inhibiting the phosphatidylinositol 3-kinase (PI3K)-AKT-mammalian target of rapamycin (mTOR) pathway. In in vitro experiments, these compounds have shown their preferential antiproliferative and cytotoxic activities in MSI-H cell lines when compared with MSS cells [Vilar et al, 2009. Clin Cancer Res 15: 2829-39].

The role of mismatch repair proteins in influencing chemosensitivity has been demonstrated, and thus it is reasonable to consider this molecular subgroup as separate entity when determining response to chemotherapy. But this molecular subgroup confers of only 15-20% of all CRC patients and can not alone explain why some patients have significant benefit from chemotherapy while others do not. Therefore a better understanding of molecular subtypes of colorectal cancers is required.

The invention provides a method of typing a sample from a colorectal cancer patient, the method comprising providing a sample from the colorectal cancer patient, whereby the sample comprises RNA expression products from a cancer cell of the patient, determining a level of RNA expression for at least two genes that are selected from Table 1C, Table 4 and/or Table 5, comparing said determined level of RNA expression of the at least two genes to the level of expression of the genes in a reference sample and typing said sample based on the comparison of the determined levels of RNA expression.

The genes depicted in Table 1 were identified in a multistep analysis of samples from colorectal cancer patients. Initial full-genome hierarchical clustering of cancer samples resulted in three distinct cancer groups (indicated as A-type, B-type and C-type) that were associated with disease progression (FIG. 1A). A number of samples showed a difference with k-means clustering outcome (FIG. 1B). These differences may indicate that the original hierarchical clustering was not entirely stable, a phenomenon that has been described previously for hierarchical clustering-based subtyping in breast cancer [Pusztai et al, 2006. Oncologist 11: 868-77]. Samples with a concordant classification between hierarchical clustering and k-means clustering were used for construction of cancer type-specific gene profiles. A 5-fold cross validation procedure within a leave-one out (LOO) cross validation loop was used for identification of cancer type-specific gene profiles and to score the classification performance compared to the initial clustering outcomes. The full-genome-based unsupervised clustering could be accurately reproduced using three dedicated gene profiles that contained only a small number of genes. Each of these gene profiles as depicted in Tables 1A-1C provides a stable means for identification of one of the three distinct cancer groups that are identified by unsupervised clustering.

C-type colorectal cancer patients had the worst outcome of the three subtypes. C-type cancer was identified in about 10-20% of all samples that were studied, which included stage I and II cancers. Patients with C-type colorectal cancer have a poor prognosis. Said at least two genes from Table 1C provides a robust gene expression signature for typing a colorectal cancer sample as a C-type colorectal sample. Said at least two genes from Table 1C predict disease relapse and may be added to current clinico-pathological risk assessment to assist physicians in making treatment decisions. C-type patients have a 5-year Distant Metastasis Free Survival (DMFS) rate of about 58%. The identification of a sub-group of patients that are more likely to suffer from a recurrent disease (distant of local metastasis) allows the identification of patients who are more likely to benefit from adjuvant chemotherapy and which, therefore, should be treated after surgery.

A method of the invention further comprising determining a stage of the cancer. The staging of a cancer is generally based on the size of the cancer and on whether the cancer has spread to lymph nodes or other areas of the body. In stages 0, I and II, the cancer has not spread to lymph nodes and no distant metastases have been identified. According to the current guidelines, stage 0 or stage I patients will not receive adjuvant chemotherapy, while the benefit of adjuvant chemotherapy for stage II colon cancer patients is still debatable [Andre et al, 2006. Ann Surg Oncol 13: 887-98]. However, C-type colorectal cancer patients having early stage colorectal cancers (stage 0, I or II) are high risk patients who should receive treatment, preferably aggressive treatment.

C-type colorectal cancer does not correlate with one of the previously established colorectal cancer types. The incidence of microsatellite instability phenotype (MSI) was about 20% (between 10 and 23%, as determined by in situ hybridization experiments of MLH1 and PMS2 markers, or by determining expression levels of MLH1 and PMS2 markers, respectively) of all identified C-type colorectal cancers. Similarly, the incidence of B-Raf mutations was about 20% of all identified C-type colorectal cancers.

In contrast, A-type cancers are enriched for MSI phenotype (between 37 and 51%) and mutations in B-Raf mutations (about 50%). B-type cancers are identified by the absence of MSI phenotype (0%) and by having no mutations in B-Raf (0%). The mutation frequency of KRAS and PI3K was found to be similar in all three cancer types. Therefore, a C-type colorectal cancer may not be identified by other means of identifying molecular subtypes of colorectal cancers.

In addition, the signature to identify patients with C-type colorectal cancer contains many genes that are potential targets for new drug and therefore might be useful in guiding new clinical studies.

The genes depicted in Tables 4 and 5 were identified in a multistep analysis of samples from colorectal cancer patients. A 10-fold cross validation procedure was used for identification of a microsatellite instability classifier. A full-genome-based analysis resulted in a set of 41 genes (Table 4) that can separate samples from MSI and MSS patients with a sensitivity of 96.6% (28/29) and a specificity of 92.7% (229/247). An analysis of a limited array comprising a part of the full-genome probes resulted in a set of 63 genes (Table 5) that can separate MSI and MSS patients with a sensitivity of 93.1% (27/29), a specificity of 87.9% (217/247) and overall accuracy 88.4% (244/276). Each of these gene profiles as depicted in Tables 4 and 5 provides a stable means for identification of MSI and MSS samples. Enriched function analysis with DAVID (Huang et al. 2009. Nat Protoc 4: 44-57.3) indicated that several of the proteins encoded by the genes in the two signatures are localized in nucleus and are involved in nucleic acids binding. This is consistent with the underlying biology that MSI phenotype is caused by deregulation of DNA mismatch repair (MMR) genes (Soreide et al. 2006. Br J Surg 93: 395-406).

A colorectal cancer patient is a patient that suffers, or is expected to suffer, from a colorectal cancer. A colorectal cancer may occur in the colon, rectum and appendix. A preferred colorectal cancer is a colon cancer.

A sample comprising RNA expression products from a cancer cell of a colorectal cancer patient is provided after the removal of all or part of a colorectal cancer sample from the patient during surgery or colonoscopy. For example, a sample comprising RNA may be obtained from a tissue sample or a biopsy sample comprising colorectal cancer cells that was previously removed by surgery. The surgical step of removing a relevant tissue sample, in this case a colorectal cancer sample, from an individual is not part of a method according to the invention.

A sample from a colorectal cancer patient comprising RNA expression products from a tumor of the patient can be obtained in numerous ways, as is known to a skilled person. For example, the sample can be freshly prepared from cells or a tissue sample at the moment of harvesting, or they can be prepared from samples that are stored at −70° C. until processed for sample preparation. Alternatively, tissues or biopsies can be stored under conditions that preserve the quality of the protein or RNA. Examples of these preservative conditions are fixation using e.g. formaline and paraffin embedding, RNase inhibitors such as RNAsin (Pharmingen) or RNasecure (Ambion), aquous solutions such as RNAlater (Assuragen; U.S. Pat. No. 6,204,375), Hepes-Glutamic acid buffer mediated Organic solvent Protection Effect (HOPE; DE10021390), and RCL2 (Alphelys; WO04083369), and non-aquous solutions such as Universal Molecular Fixative (Sakura Finetek USA Inc.; US7138226). Alternatively, a sample from a colorectal cancer patient may be fixated in formalin, for example as formalin-fixed paraffin-embedded (FFPE) tissue.

RNA may be isolated from isolated from a colorectal tissue sample by any technique known in the art, including but not limited to Trizol (Invitrogen; Carlsbad, Calif.), RNAqueous® (Applied Biosystems/Ambion, Austin, Tx), Qiazol (Qiagen, Hilden, Germany), Agilent Total RNA Isolation Lits (Agilent; Santa Clara, Calif.), RNA-Bee (Tel-Test. Friendswood, Tex.), and Maxwell™ 16 Total RNA Purification Kit (Promega; Madison, Wis.). A preferred RNA isolation procedure involves the use of Qiazol (Qiagen, Hilden, Germany).

The level of RNA expression of at least two of the genes of Table 1A, 1B and 1C and/or Tables 4 and 5 can be determined by any method known in the art. Methods to determine RNA levels of genes are known to a skilled person and include, but are not limited to, Northern blotting, quantitative PCR, and microarray analysis and RNA sequencing. A preferred method for determining a level of RNA expression is microarray analysis.

Each of the genes in Table 1C has an Area Under the Receiver Operation Curve (AUC) of at least 0.789. This indicates that each of these genes has a high diagnostic accuracy for distinguishing C-type colorectal cancers from other colorectal cancers. In one embodiment, said at least two genes that are selected from Table 1C preferably comprise the two genes that have the highest AUC. Therefore, in this embodiment, said at least two genes comprise CD248 and COL6A3.

In a further embodiment, it is preferred that at least one of the at least two genes selected from Table 1C is a gene that is upregulated in a Type C colorectal cancer and at least one further gene is downregulated in a Type C colorectal cancer, compared to the level of expression in the reference sample. Said upregulated gene is preferably selected from COX7A1, BNC2, COL18A1, SLIT3, MXRA8, MAP3K3, COL6A3, CD248, BASP1, and LAMB2, being the genes with the highest AUC. Said downregulated gene is preferably selected from DIAPH3, FBXO5, SPBC25, NDUFAB1, XRCC2, RFC4, SYNCRIP, SNRPC, TOM1L1 and NDUFA10 being the genes with the highest AUC.

Said at least two genes selected from Table 1C are more preferred based on the differential expression of the gene in a type C-colorectal sample versus the reference sample. According to this embodiment, said upregulated gene is preferably selected from THBS2, SPOCK1, COL5A2, FBLN1, MGP, MXRA8, DCN, AEBP1, BASP1, and COL6A1. Said downregulated gene is preferably selected from DIAPH3, SPBC25, NIPSNAP1, ZNF367, ORC6L, ASPM, FBXO5, PPARA, ZNF695 and RFC4.

A most preferred gene that is upregulated in a Type C colorectal cancer is THBS2. A most preferred gene that is downregulated in a Type C colorectal cancer is DIAPH3.

A preferred method according to the invention comprises determining a level of RNA expression for at least three genes that are selected from Table 1C, more preferred at least four genes that are selected from Table 1C, more preferred at least five genes that are selected from Table 1C, more preferred at least six genes that are selected from Table 1C, more preferred at least seven genes that are selected from Table 1C, more preferred at least eight genes that are selected from Table 1C, more preferred at least nine genes that are selected from Table 1C, more preferred at least ten genes that are selected from Table 1C, more preferred at least fifteen genes that are selected from Table 1C, more preferred at least twenty genes that are selected from Table 1C, more preferred at least fifty genes that are selected from Table 1C, more preferred at least seventy-five genes that are selected from Table 1C, more preferred at least hundred that are selected from Table 1C.

In a further preferred embodiment, a method of the invention comprises determining a level of RNA expression for all 102 genes of Table 1C.

A further preferred method according to the invention further comprises determining a level of RNA expression for at least two genes that are selected from Table 1A and at least two genes that are selected from Table 1B. Said at least two genes from Table 1A provide a robust gene expression signature for typing a colorectal cancer sample as an A-type colorectal sample. Said at least two genes from Table 1B provide a robust gene expression signature for typing a colorectal cancer sample as a B-type colorectal sample.

A-type cancers are enriched for cancer cells with an MSI phenotype (p<0.000) and cancer cells with BRAF mutations (p=0.03). Patients of the A-type have an excellent prognosis to stay disease-free with a 5-year disease and metastasis-free survival rate of 97.1% (95% coincidence interval between 91.5-100%). B-type cancers are identified by the absence of MSI phenotype (0%) and by having no mutations in B-Raf (0%). B-type patients have an intermediate prognosis with a 5-year disease and metastasis-free survival rate of 80.2%.

Each of the genes in Table 1A has an area under the curve (AUC) of at least 0.678. This indicates that each of these genes has a high diagnostic accuracy for distinguishing A-type colorectal cancers from other colorectal cancers. In one embodiment, said at least two genes that are selected from Table 1A preferably comprise the two genes that have the highest AUC. Therefore, in this embodiment, said at least two genes comprise SORBS1 and AS3MT. In a further embodiment, it is preferred that at least one of the at least two genes selected from Table 1A is a gene that is upregulated in a Type A colorectal cancer and at least one further gene is downregulated in a Type A colorectal cancer, compared to the level of expression in the reference sample. Said upregulated gene is preferably selected from HSPA4L, NUDT6, ECHS1, ME1, MREG, URM1, NIPA1, KNTC2, PRC1, and ACADSB, being the genes with the highest AUC.

Said downregulated gene is preferably selected from AS3MT, SORBS1, NRXN1, SNX21, DKFZp547K054, ARFGAP1, FCGRT, RGN, SRPX2, RARA, being the genes with the highest AUC.

Said at least two genes selected from Table 1A are more preferred based on the differential expression of the gene in a type A-colorectal sample versus the reference sample. According to this embodiment, said upregulated gene is preferably selected from HSPA4L, SLC7A11, NUDT6, ME1, DLG7, KNTC2, PRC1, ECHS1, DEPDC1, and ACADSB. Said downregulated gene is preferably selected from SRPX2, RP4-691N24.1, FHOD3, LARP6, FCGRT, SORBS1, CTSF, RGN, DKFZp547K054, and AS3MT.

A most preferred gene that is upregulated in a type A colorectal cancer is HSPA4L. A most preferred gene that is downregulated in a type A colorectal cancer is SRPX2. A preferred method according to the invention comprises HSP4L and SRPX2 from Table 1A, in addition to at least two genes from Table 1C.

A further preferred method according to the invention comprises all 32 genes listed in Table 1A, in addition to at least two genes from Table 1C.

Each of the genes in Table 1B has an AUC of at least 0.794. This indicates that each of these genes has a high diagnostic accuracy for distinguishing B-type colorectal cancers from other colorectal cancers. In one embodiment, said at least two genes that are selected from Table 1B preferably comprise the two genes that have the highest AUC. Therefore, in this embodiment, said at least two genes comprise BG114486 and PLAGL2.

In a further embodiment, it is preferred that at least one of the at least two genes selected from Table 1B is a gene that is upregulated in a Type B colorectal cancer and at least one further gene is downregulated in a Type B colorectal cancer, compared to the level of expression in the reference sample. Said upregulated gene is preferably selected from BG114486, LAGL2, TSPAN6, PIGU, SLC6A4, POFUT1, VAPB, VAV3, QPRT, and C20orf142, being the genes with the highest AUC.

Said downregulated gene is preferably selected from LOC388610, RAMP1, PLK2, TRIB2, KCTD1, SLC41A1, MAPRE2, and EPOR, being the genes with the highest AUC.

Said at least two genes selected from Table 1B are more preferred based on the differential expression of the gene in a type B-colorectal sample versus the reference sample. According to this embodiment, said upregulated gene is preferably selected from BG114486, THC2669157, QPRT, PLA2G12B, VAV3, PTPRO, RNF43, DDC, AXIN2, and C13orf18. Said downregulated gene is preferably selected from LOC388610, RAMP1, PLK2, TRIB2, KCTD1, SLC41A1, MAPRE2, and EPOR.

A most preferred gene that is upregulated in a type B colorectal cancer is BG114486. A most preferred gene that is downregulated in a type B colorectal cancer is LOC388610. A most preferred method according to the invention comprises BG114486 and LOC388610 from Table 1B, in addition to at least two genes from Table 1C.

A further preferred method according to the invention comprises all 53 genes listed in Table 1B, in addition to at least two genes from Table 1C.

A further preferred method according to the invention comprises all 53 genes listed in Table 1B, in addition to at least two genes from Table 1C and at least two genes from Table 1A.

A further preferred method according to the invention comprises all 32 genes listed in Table 1A, all 53 genes listed in Table 1B and all 102 genes listed in Table 1C.

Each of the genes in Tables 4 and 5 have a P-value that is lower than $1.58 \, E^{08}$. This indicates that each of these genes has a high diagnostic accuracy for distinguishing samples from MSI and MSS colorectal cancer patients. In one embodiment, said at least two genes that are selected from Tables 4 and/or 5 preferably comprise the two genes that have the lowest P-value. Therefore, in this embodiment, said at least two genes comprise DUSP18 and SMCR7L.

A preferred method according to the invention comprises determining a level of RNA expression for at least three genes that are selected from Tables 4 and/or 5, more preferred at least four genes that are selected from Tables 4 and/or 5, more preferred at least five genes that are selected from Tables 4 and/or 5, more preferred at least six genes that are selected from Tables 4 and/or 5, more preferred at least seven genes that are selected from Tables 4 and/or 5, more preferred at least eight genes that are selected from Tables 4 and/or 5, more preferred at least nine genes that are selected from Tables 4 and/or 5, more preferred at least ten genes that are selected from Tables 4 and/or 5, more preferred at least fifteen genes that are selected from Tables 4 and/or 5, more preferred at least twenty genes that are selected from Tables 4 and/or 5, more preferred all genes from Tables 4 and/or 5.

A more preferred combination of genes selected from Table 4 and/or 5 is provided by DUSP18 and SMCR7L, more preferred DUSP18, SMCR7L and CEP68, more preferred DUSP18, SMCR7L, CEP68 and UNKL, more preferred DUSP18, SMCR7L, CEP68, UNKL and KCNK5, more preferred DUSP18, SMCR7L, CEP68, UNKL, KCNK5 and RNF43, more preferred DUSP18, SMCR7L, CEP68, UNKL, KCNK5, RNF43 and RPL22L1, more preferred DUSP18, SMCR7L, CEP68, UNKL, KCNK5, RNF43, RPL22L1 and AXIN2, more preferred DUSP18, SMCR7L, CEP68, UNKL, KCNK5, RNF43, RPL22L1, AXIN2 and TNNC2, more preferred DUSP18, SMCR7L, CEP68, UNKL, KCNK5, RNF43, RPL22L1, AXIN2, TNNC2, and ATP9A, more preferred DUSP18, SMCR7L, CEP68, UNKL, KCNK5, RNF43, RPL22L1, AXIN2, TNNC2, ATP9A and VAV3, more preferred DUSP18, SMCR7L, CEP68, UNKL, KCNK5, RNF43, RPL22L1, AXIN2, TNNC2, ATP9A, VAV3 and QPRT, more preferred DUSP18, SMCR7L, CEP68, UNKL, KCNK5, RNF43, RPL22L1, AXIN2, TNNC2, ATP9A, VAV3, QPRT and PLAGL2, more preferred DUSP18, SMCR7L, CEP68, UNKL, KCNK5, RNF43, RPL22L1, AXIN2, TNNC2, ATP9A, VAV3, QPRT, PLAGL2, and C13orf18, more preferred DUSP18, SMCR7L, CEP68, UNKL, KCNK5, RNF43, RPL22L1, AXIN2, TNNC2, ATP9A, VAV3, QPRT, PLAGL2, C13orf18 and ARID3A. A combination of genes from genes selected from Table 4 and/or 5 may be combined with MLH1 (NM_000249), which is downregulated in MSI patients when compared to MSS patients.

It is further preferred that the level of expression of at least two of the genes in Table 4 and/or 5 is compared to the level of expression in a reference sample.

A reference sample is preferably a sample comprising RNA expression products from a cell, preferably a colorectal cell. Said colorectal cell may be isolated from a colorectal tissue of a healthy individual, or from a relevant cell line or mixture of cell lines. Said reference sample preferably comprises RNA expression products from a primary cancer tissue from one or more colorectal cancer patients. The RNA from a cell line or cell line mixture can be produced in-house or obtained from a commercial source such as, for example, Human Reference RNA (Stratagene). A most preferred reference sample comprises a pool of RNA expression products from primary cancer tissues from more than ten colorectal cancer patients, more preferred more than twenty colorectal cancer patients, more preferred more than thirty colorectal cancer patients, more preferred more than forty colorectal cancer patients. Said colorectal cancer patients may be selected from patients with a low risk of cancer recurrence or an increased risk of cancer recurrence and/or from MSI and MSS colorectal cancer patients. A preferred reference sample comprises RNA expression products from colorectal cancer tissue from patients with a low and an increased risk of cancer recurrence.

As an alternative, a static reference can be generated which enables performing single channel hybridizations. A preferred static reference is calculated by measuring the median background-subtracted level of expression (rMean-Signal) of a gene across 5 hybridizations of a reference sample, preferably obtained from pooled colorectal cancer samples, on a microarray. The level of expression may be normalized as is known a skilled person. Subsequently, log-ratios for each gene/probe hybridization is generated relative to the value of the static reference.

A preferred method according to the invention further comprises normalizing the determined RNA levels of the at least two genes in the colorectal sample to correct for systemic bias. Systemic bias can be introduced, for example, during handling of the sample. To reduce systemic bias, the determined levels of RNA expression are corrected for background non-specific reactions. For this, the levels of expression of so-called house-keeping genes are used to correct for systemic differences between samples.

Systemic bias in microarray analyses results in variation by inter-array differences in overall performance, which can be due to for example inconsistencies in array fabrication, staining and scanning, and variation between labeled RNA samples, which can be due for example to variations in purity. Normalization of microarray data is preformed, for example, with Feature Extraction software (Agilent Technologies). Other methods that are or will be known to a person of ordinary skill in the art, such as a dye swap experiment (Martin-Magniette et al., Bioinformatics 21:1995-2000 (2005)) can also be applied to normalize for systemic bias.

Normalization of the expression levels results in normalized expression values. Normalization preferably comprises median centering, in which the "centers" of hybridization peaks are brought to the same level under the assumption that the majority of genes are un-changed between experiments. Said normalization preferably comprises Lowess (LOcally WEighted Scatterplot Smoothing) local regression normalization to correct for both print-tip and intensity-dependent bias.

Typing of a colorectal tumor sample comprises determination of a normalized level of RNA expression of said at least two genes, and calculation of a set of scores or indexes that quantifies the studied sample. Said normalized level of RNA expression is preferably determined as (log-)ratio compared to the values that have been determined in said reference sample.

Typing of a sample can be performed in various ways. In one method, a coefficient is determined that is a measure of a similarity or dissimilarity of a sample with a previously established gene pattern that is specific of a certain cell type, tissue, disease state or any other interesting biological or clinically-relevant sample or group of samples. A specific gene expression pattern in a specific cell type, tissue, disease state or any other interesting biological or clinically-relevant sample or group of samples is termed a "profile template". Typing of a sample can be based on its (dis)similarity to a single profile template or based on multiple profile templates. In the invention, the profile templates are representative for A-, B- and C-type colon cancer. Said profile template is herein also termed a "gene signature" or "gene profile".

A number of different coefficients can be used for determining a correlation between the RNA expression level in a sample from a colorectal cancer patient and a reference sample. Preferred methods are parametric methods which assume a normal distribution of the data. Preferred methods comprise cosine-angle, un-centered correlation and, cosine correlation (Fan et al., Conf Proc IEEE Eng Med Biol Soc. 5:4810-3 (2005)). More preferred is the Pearson product-moment correlation coefficient, which is obtained by dividing the covariance of the two variables by the product of their standard deviations. Preferably, said correlation with a profile template is used to produce an overall similarity score for the set of genes that are used. A similarity score is a measure of the average correlation of RNA levels of a set of genes in an RNA sample from an individual and a profile template. Said similarity score can, for example, be a numerical value between +1, indicative of a high correlation between the RNA expression level of said set of genes in a RNA sample of said individual and said profile template, and −1, which is indicative of an inverse correlation. Preferably, an arbitrary threshold is used to type samples as A-type colon cancer, B-type colon cancer or C-type colon cancer. More preferably, samples are classified as A-, B- or C-type colon cancer based on the respective highest similarity measurement. A similarity score is preferably displayed or outputted to a user interface device, a computer readable storage medium, or a local or remote computer system.

A method according to the invention preferably further comprises assessment of clinical information, such as tumor size, tumor grade, lymph node status and family history. Clinical information may be determined in part by histopathologic staging. Histopathologic staging involves determining the extent of spread through the layers that form the wall of the colon/rectum, combined with determining of the number of lymph nodes that are affected by the cancer, and/or whether the cancer has spread to a distant organ. A preferred staging system is the TNM (for tumors/nodes/metastases) system, from the American Joint Committee on Cancer (AJCC). The TNM system assigns a number based on three categories. "T" denotes the degree of invasion of the intestinal wall, "N" the degree of lymphatic node involvement, and "M" the degree of metastasis. Stage 0 indicates a cancer that is confined to the mucosa. Stage I indicates a cancer that has not invaded the layer of tissue under the serosa. Stage II indicates a cancer that has invaded the subserosa and adjacent organs but without affecting regional lymph nodes and no distant metastasis. Stage III indicates a cancer that has affected regional lymph nodes without distant metastasis. Stage 1V indicates the presence of distant metastasis. The method described here is stage independent and applies to all colorectal cancers.

A method according to the invention preferably in addition comprises determining a metastasizing potential of the cancer. Said metastasizing potential is preferably determined by molecular expression profiling. Molecular expression profiling may be used instead of clinical assessment or, preferably, in addition to clinical assessment. Molecular expression profiling may facilitate the identification of patients who may be safely managed without adjuvant chemotherapy. A preferred molecular expression profiling is described in WO2010/074573 [Salazar et al. 2010 JCO 28 Nov. 22. Epub ahead of print].

A method according to the invention preferably further comprises determining a strategy for treatment of the patient. Treatment may include, for example, radiation therapy, chemotherapy, targeted therapy, or some combination thereof. Treatment decisions for individual colorectal cancer patients are currently based on stage, patient age and condition, the location and grade of the cancer, the number of patient lymph nodes involved, and the absence or presence of distant metastases.

Typing of colorectal cancers into a molecular subtype at the time of diagnosis using the methods disclosed herein provides an additional or alternative treatment decision-making factor. The methods of the invention permit the differentiation of three types of colorectal cancers, termed A-type, B-type and C-type, and the differentiation of MSI-like versus MSS colorectal cancers. A-type patients have a good prognosis, B-type patients an intermediate prognosis, and C-type patients a poor prognosis. MSI-like patients have a good prognosis, while MSS patients have a poor prognosis. The methods of the invention find particular use in choosing appropriate treatment for early-stage colorectal cancer patients.

The majority of colorectal cancer patients diagnosed at an early-stage of the disease enjoy long-term survival following surgery without further therapy. In general, A-type and/or B-type type patients and MSI-like patients with an early disease stage (TNM 0, TNM I or TNM II) will not benefit from adjuvant chemotherapy. However, it was surprisingly found that stage 2 patients showed a benefit of chemotherapy for patients with a A-type colon tumor (+16.9% 10 years DMFS), compared to B-type (−3.5%) and C-type (+0.1%) stage 2 patients. In addition, treatment may be assigned to a patient with a type C sample with stage 3 and to a patient with a type B sample with stage 3.

Moreover, early stage A-type and/or B-type type patients that have a poor prognosis, as determined by molecular expression profiling, may benefit from adjuvant therapy (e.g., radiation therapy or chemotherapy). Chemotherapy for these early stage patients may include fluorouracil (5-FU), 5-FU plus leucovorin (folinic acid); 5-FU, leucovorin plus oxaliplatin; 5-FU, leucovorin plus irinotecan; capecitabine, and/or drugs for targeted therapy, such as an anti-VEGF antibody, for example Bevacizumab, and an anti-Epidermal growth factor receptor antibody, for example Cetuximab. Radiation therapy may include external and/or internal radiation therapy. Radiation therapy may be combined with chemotherapy as adjuvant therapy.

Irrespective of staging and/or prognosis, as determined by molecular expression profiling, C-type patients and MSS patients are more likely to benefit from adjuvant chemotherapy. The methods of the present invention find use in identifying this high-risk, poor prognosis population of early-stage colorectal cancer patients and thereby determining which patients would benefit from continued and/or more aggressive therapy and close monitoring following treatment.

The determination of the MSI status of a colorectal cancer has clinical use for identifying patients with HNPCC/Lynch Syndrome. In addition, MSI status may be used in therapeutic decision-making. Although MSI colorectal cancers are associated with favorable prognosis, there is evidence that patients with MSI colorectal cancers respond differently to fluorouracil-based chemotherapy compared to patients with MSS colorectal cancers. Especially patients with stage 2 MSI colorectal cancers may be harmed by treatment with 5-FU. It was therefore recommended to test for MSI in all stage 2 colon cancer patients, and not to prescribe 5-FU to MSI-high patients with stage 2 colon cancer. Therefore, the identification of MSI-like samples by the methods of the invention, which samples were typed as MSS samples by standard methods (IHC/PCR), is of high clinical relevance. It is preferred that patients with stage 2 type A and/or stage 2 MSI-like colorectal cancer are not treated with 5-FU.

The methods for typing a C-type colorectal cancer according to the invention preferably further comprise determining a strategy for treatment of the patient that is based on the level of expression of at least one of the genes depicted in Table 1C. The genes depicted in Table 1C contain many potential targets for a new drug and therefore might be useful in guiding new clinical studies.

Figure 5:
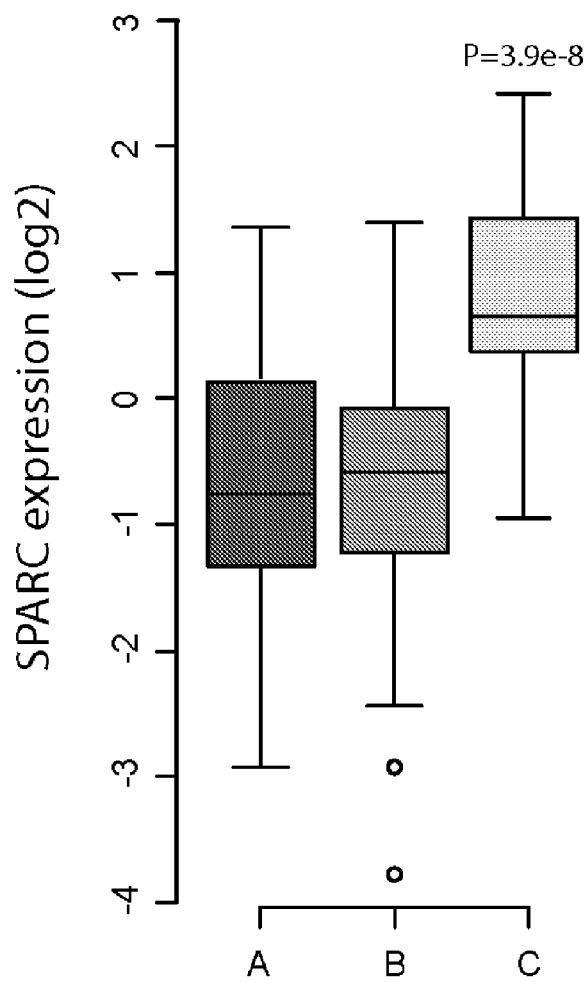

For example, the secreted protein acidic and rich in cysteine/osteonectin/BM40 (SPARC) is one of the genes that is upregulated in C-type colorectal cancers (see FIG. 5). Upregulation of SPARC may correlate with a positive response to nab-paclitaxel, as shown in early phase clinical studies (Desai et al. 2008. Anticancer Drugs 19: 899-909; Desai et al. 2009. Transl Oncol 2: 59-64). Therefore, a poor prognosis SPARC-positive C-type patient may benefit from treatment with nab-paclitaxel.

In addition, several other genes that are upregulated in C-type colorectal cancers comprise interesting new drug targets. For example, janus kinases (JAK) are a small family of receptor-associated kinases, that together with signal transducers and activators of transcription (STAT), provide a rapid signalling pathway for cytokines. JAK3 has recently been identified as a potential drug target for treatment of cancer (patent application U.S. Ser. No. 12/374,524). Claudin 5 (CLDN5) is an integral membrane protein and a component of tight junction strands. First results with monoclonal antibodies indicate that claudin targeting may be a novel strategy for inhibiting tumor metastases [Kato-Nakano et al. 2010 Anticancer Res. 30: 4555-62]. FLT4, or fms-related tyrosine kinase 4 or VEGFR-3, encodes a tyrosine kinase receptor for vascular endothelial growth factors C and D. Multiple small-molecule, multi-targeted receptor tyrosine kinase (RTK) inhibitor (like e/g. Sunitinib, pazopanib, CEP 7055, KRN-951, telatinib, sorafenib are developed and tested in various cancers. Fibroblast Growth Factor receptor 1 (FGFR1) consists of an extracellular region, composed of three immunoglobulin-like domains, a single hydrophobic membrane-spanning segment and a cytoplasmic tyrosine kinase domain. Recent studies have shown that Brivanib, a selective dual inhibitor of FGF and VEGF signaling, demonstrates antitumor activity in a broad range of xenograft models. Pazopanib is a potent and selective multi-targeted receptor tyrosine kinase inhibitor that might inhibit FGFR1 [Gotink and Verheul 2010. Angiogenesis 13: 1-14]. Mitogen-activated protein kinase kinase kinase 3 (MAP3K3) directly regulates the stress-activated protein kinase (SAPK) and extracellular signal-regulated protein kinase (ERK) pathways by activating SEK and MEK1/2 respectively. Several MAP-Kinase inhibitors are currently in clinical studies to study their potential to inhibit cancer progression. Platelet-derived growth factor receptor (PDGFR) is a cell surface tyrosine kinase receptor for members of the platelet-derived growth factor family and investigated as new drug targets in cancer (e.g. dasatinib, sunitinib, pazopanib, axitinib, KRN-951, tandutinib, imatinib, sorafenib, becaplermin) [Dai 2010 Expert Opin Ther Pat 20: 885-97]. Tubulin 6 (TUBB6), a β-tubulin, is one of the proteins that make up microtubules. Microtubules serve as structural components within cells and are involved in many cellular processes including mitosis, cytokinesis, and vesicular transport Tubulins are targets for anticancer drugs like Taxol, Tesetaxel and the "Vinca alkaloid" drugs such as vinblastine and vincristine. XRCC2 encodes a member of the RecA/Rad51-related protein family that participates in homologous recombination to maintain chromosome stability and repair DNA damage. In addition, a naturally occurring genetic variant of human XRCC2 confers increased resistance to cisplatin-induced DNA damage, indicating that this gene is essential for the response to cisplatin. XRCC2 is down-regulated in C-type patients which might lead to increased sensitivity to cisplatin-induced DNA damage.

Therefore, a colorectal cancer patient having a C-type cancer may benefit from adjuvant therapy comprising a drug that targets one or more of the genes depicted in Table 1C. Said drug may be provided in addition to adjuvant chemotherapy as indicated hereinabove, or in stead of the indicated chemotherapy.

The invention further provides a method of assigning treatment to a patient suffering from colorectal cancer, comprising (a) typing a relevant sample from the patient according to the methods of invention comprising at least 2 genes from Table 1A, at least two genes from Table 1B and at least two genes from Table 1C; (b) classifying said sample as a type A sample, a type B sample or a type C sample; (c) assigning treatment to an individual of which the sample is classified as a type C sample.

The invention further provides a method of assigning treatment to a patient suffering from colorectal cancer, comprising (a) typing a relevant sample from the patient according to the methods of invention comprising at least 2 genes from Table 1A, at least two genes from Table 1B and at least two genes from Table 1C; (b) classifying said sample as a type A sample, a type B sample or a type C sample; (c) determining a metastasizing potential of the sample; (d) assigning treatment if the sample is classified as a type A or type B sample with a high metastasizing potential.

The invention further provides a method of assigning treatment to a patient suffering from colorectal cancer, comprising (a) typing a relevant sample from the patient according to the methods of invention comprising at least 2 genes from Table 4 and/or Table 5; (b) classifying said sample as a MSI-like or MSS; (c) assigning treatment to an individual of which the sample is classified as MSS.

The invention further provides a method of assigning treatment to a patient suffering from colorectal cancer, comprising (a) determining a stage of the colorectal cancer, (b) typing a relevant sample from the patient according to the method of claim 1 or claim 5; (c) classifying said sample as MSI-like or MSS; (d) not assigning treatment with 5-FU if the sample is classified as stage 2 and MSI-like.

FIGURE LEGENDS

FIG. 1. Unsupervised Clustering Indicates Three Main Colon Tumor Subgroups.

(A) Full-genome hierarchical clustering (HC) of 188 colon tumors indicates three separate groups. (B) K-means (k=3) clustering (kMC) outcomes based on a 5-fold CV procedure. The likely-hood score is based on 100×100 CV iterations in which 500 randomly chosen are used for kMC. This final kMC outcome is based on the majority vote. Samples are ordered according to the HC in A.

Figure 2A:
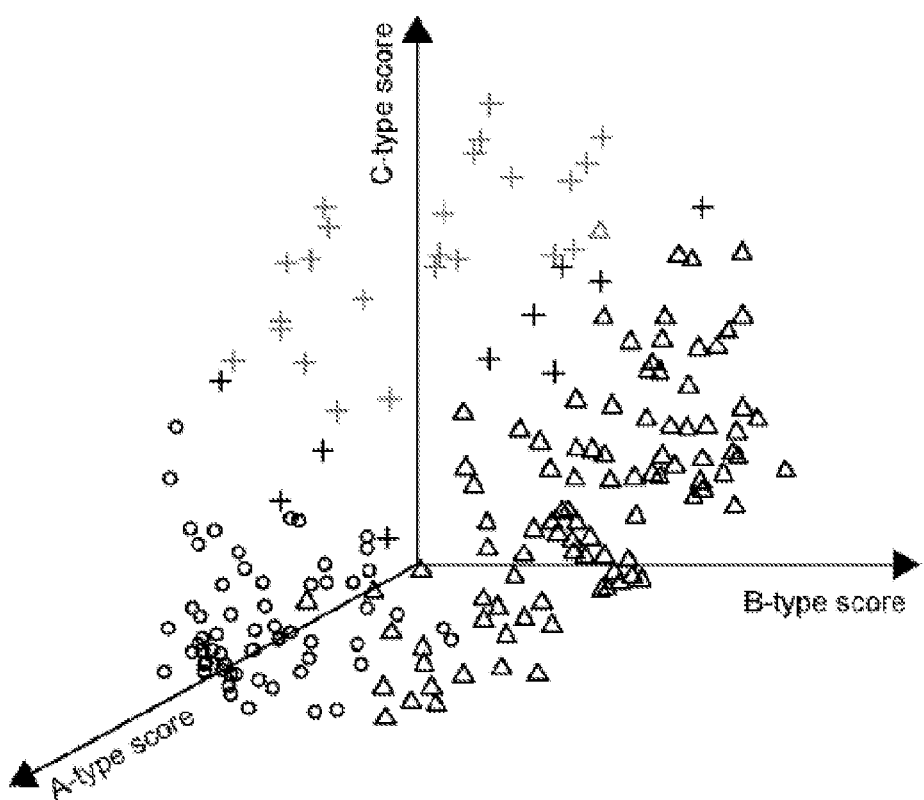
Figure 2B:
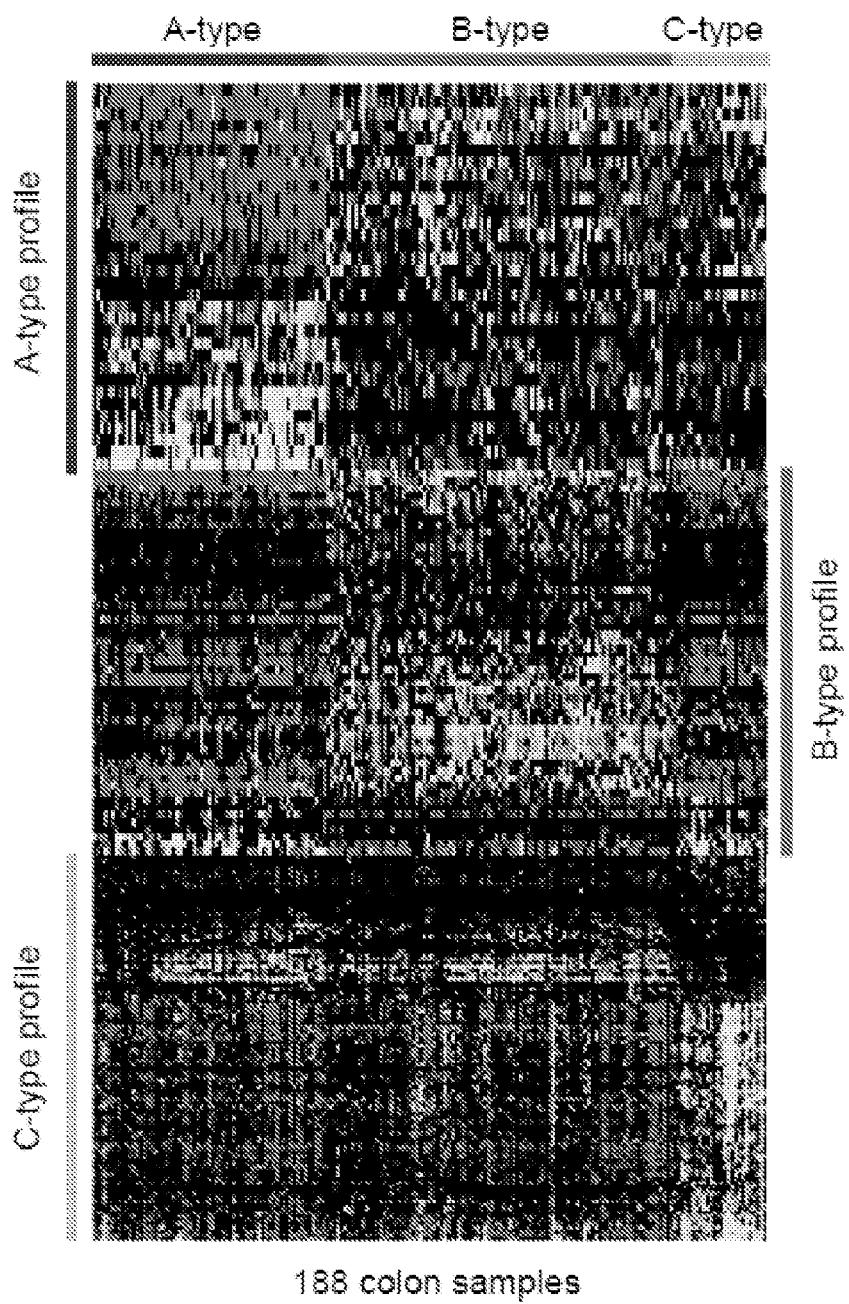

FIG. 2. Colon Molecular Subtype (CMS) Classification of 188 Tumor Samples.

(A) 3D-scatterplot is shown for all 188 studied colon tumor samples. The y, x and z-axis respectively show the A-type, B-type and C-type classification scores. Samples are colored according to their CMS classification in which A-types are shown in dark gray, B-types in gray and C-types in light gray. The plotted symbol are according to the unsupervised kMC classification in which clusters A, B and C are represented by circles, triangles and crosses, respectively. (B) Heatmap showing the three subtype profiles for the studied 188 samples. Tumors are ordered according to their CMS classification and genes are grouped for the subtype specific profiles.

Figure 3:
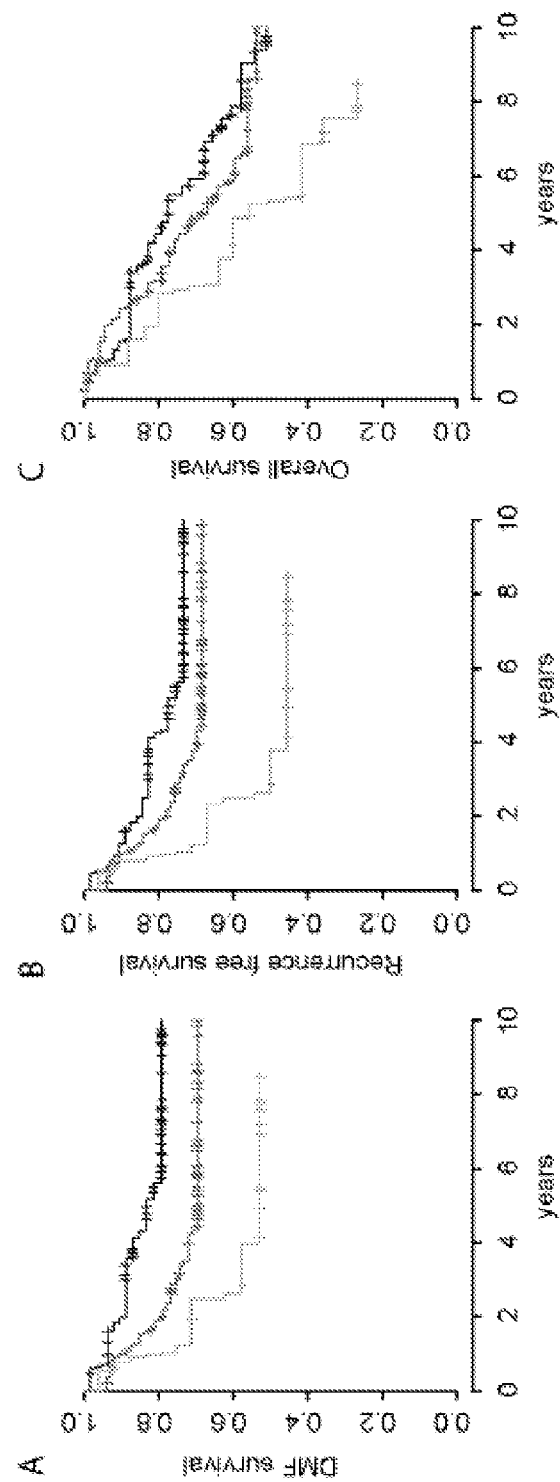

FIG. 3. Kaplan-Meier Survival Analysis of Outcome in the Three Molecular Subtypes.

Metastasis-free (A), recurrence-free (B) and overall survival (C) of the A, B and C-type colon samples are indicated by the dark gray, gray and light gray curves, respectively.

Figure 4:
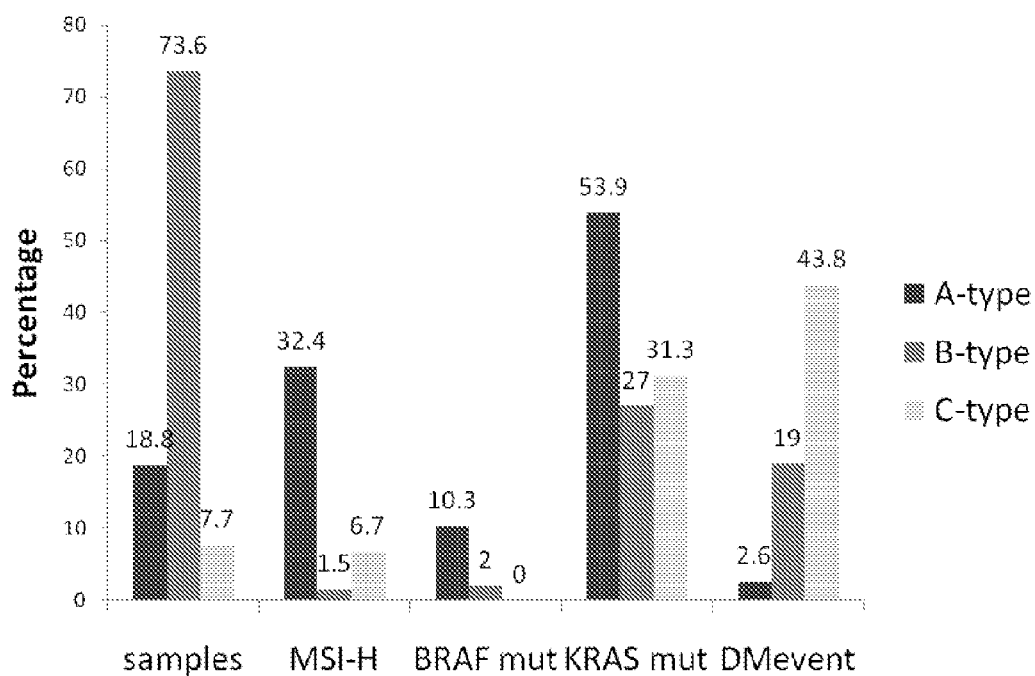

FIG. 4. Independent Validation of Molecular Subtype Signature in Patients from a Different Hospital n=208.

Using the molecular characteristics described for the training set, the independent validation confirms the difference of the molecular subtypes. The A-type is enriched for MSI-H patients and patients with BRAF mutations and has a good outcome (shown as low number of Distant metastasis DM) while the B-type has a mediate prognosis and the C-type a very poor prognosis.

FIG. 5. SPARC Expression in Molecular Subtypes.

Boxplots of relative expression of SPARC across the three colon molecular subtypes subtypes.

Figure 6:
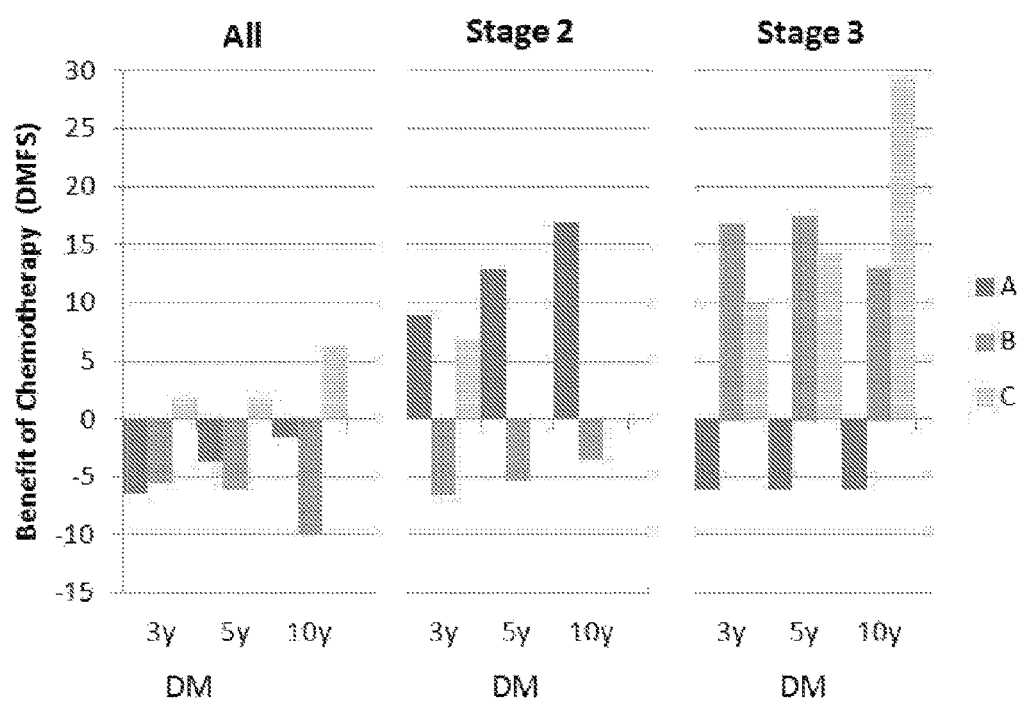

FIG. 6. Chemotherapy Benefit Across the Colon Molecular Subtypes

Benefit of chemotherapy across the three molecular subtypes as measured by the difference in DMFS rates between treated and untreated patients.

Figure 7:
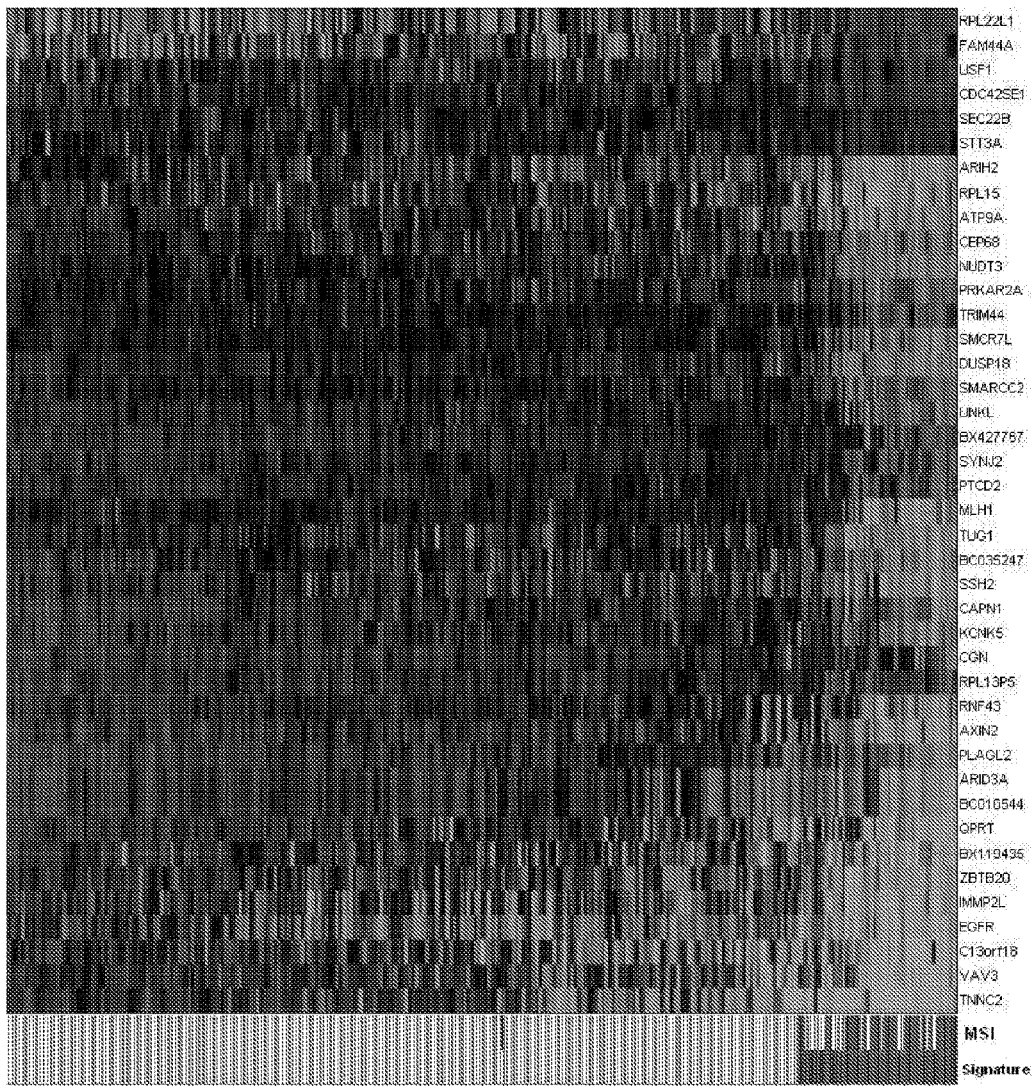

FIG. 7. Heatmap of 41-gene MSI signature. MSI row: black indicates MSI, white indicates MSS. Signature row: black indicates tumor that predicted as MSI-like.

Figure 8:
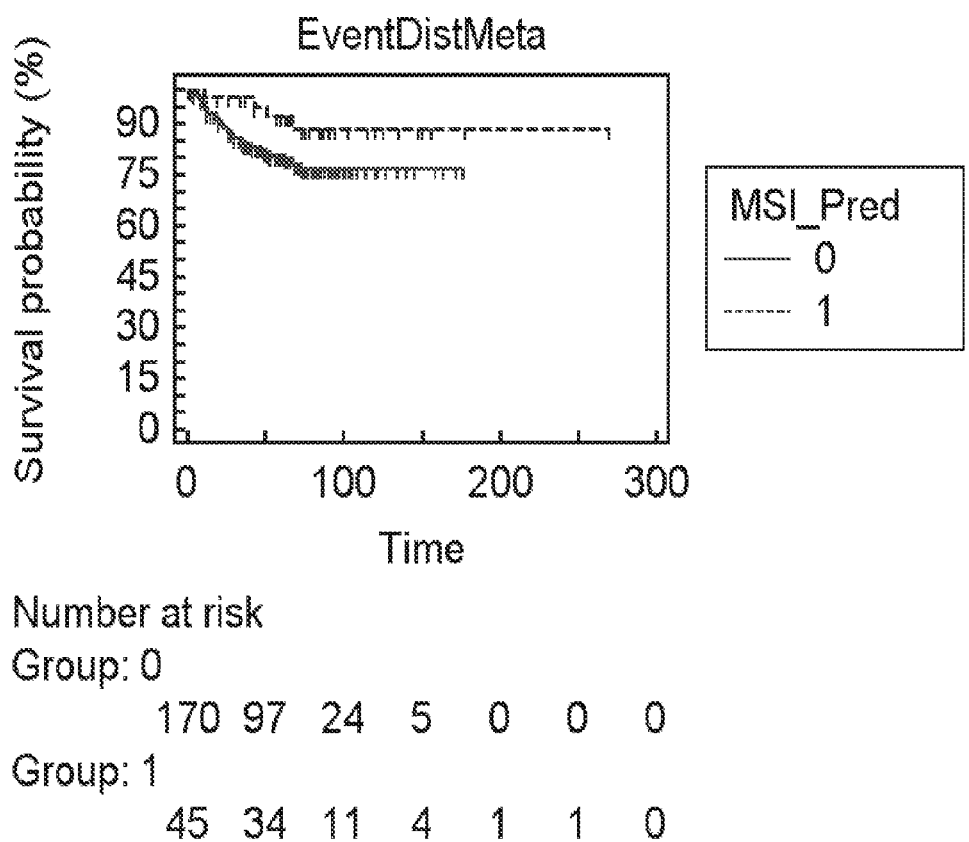

FIG. 8. Prognostic value (p=0.08) of the 41-gene signature on 215 stage 2 colorectal cancer patients.

Figure 9:
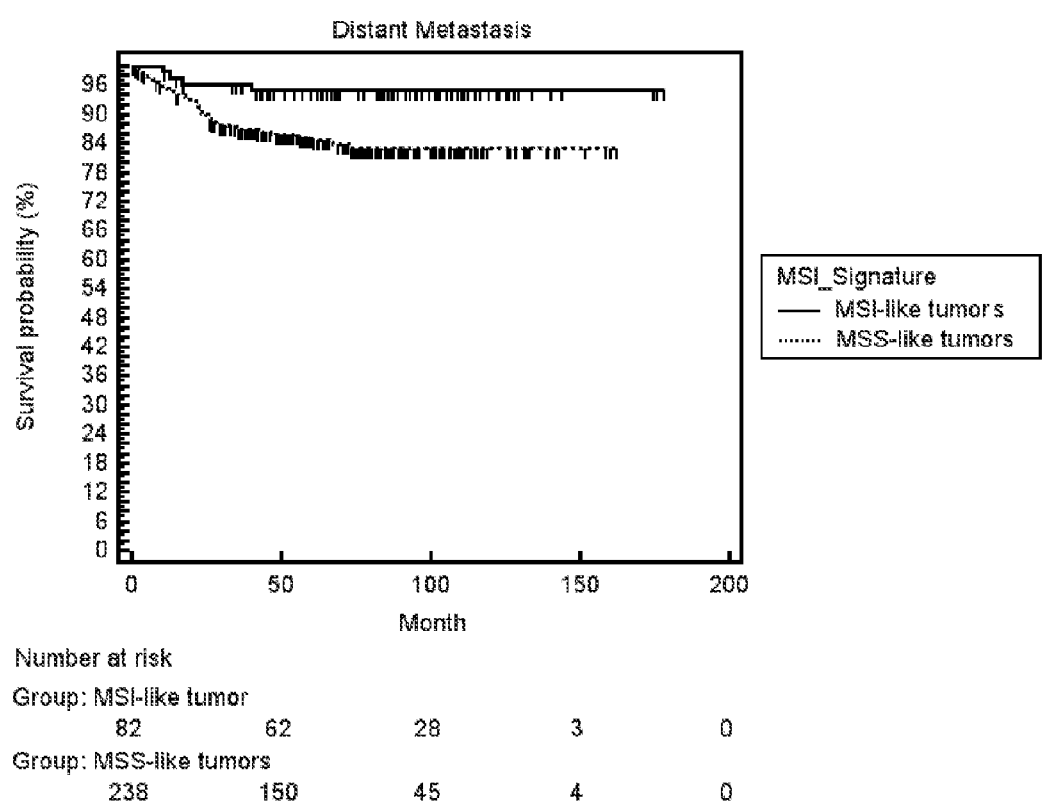

FIG. 9. Prognostic value of the 63-genes signature was validated on 320 samples of stage 2 patients from five different patients cohorts. The 63-genes signature showed significant prognostic value (p=0.015, HR=3.33, 95% CI 1.66-6.69).

Figure 10:
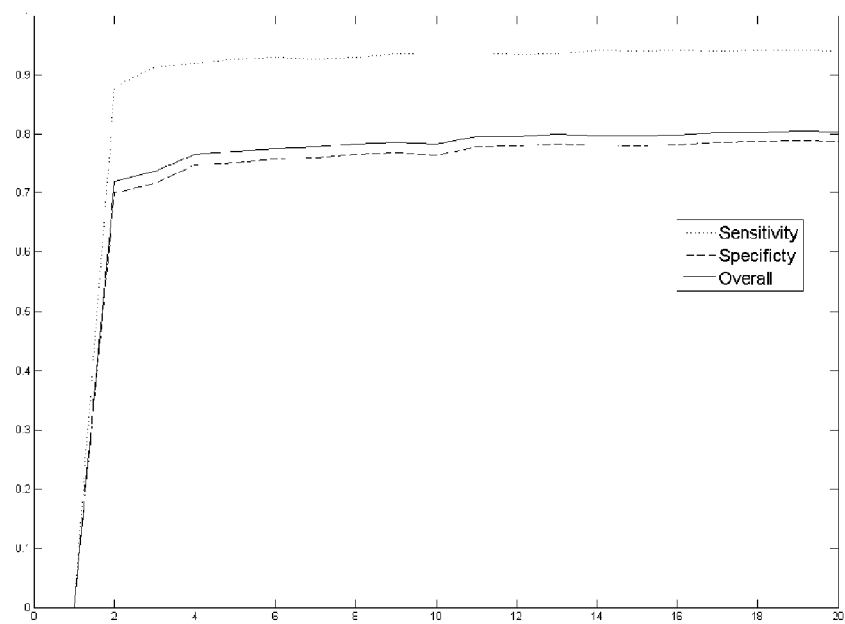

FIG. 10. The minimal number of random combination of 2 genes out of 63-genes can already achieve above 70% overall accuracy.

Figure 11:
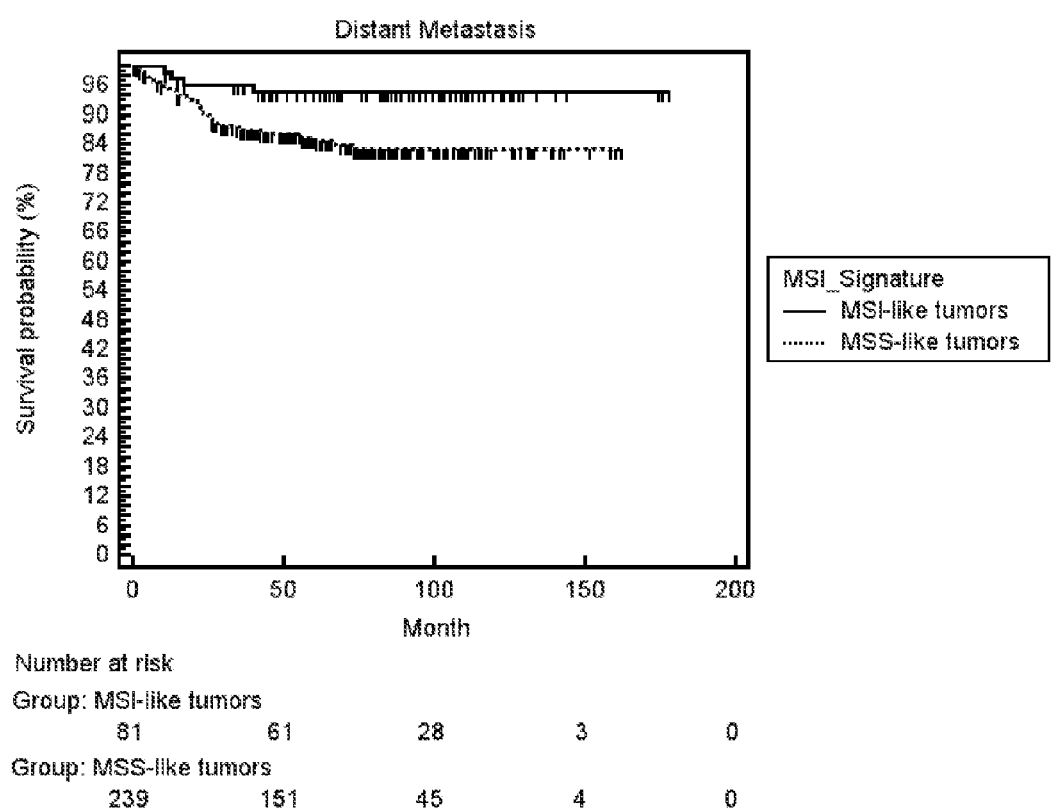

FIG. 11. Prognostic value of 64-genes signature on a 320 samples of stage 2 patients from five different patients cohorts. The 64-genes signature showed significant prognostic value (p=0.02, HR=3.27, 95% CI 1.62-6.59).

Figure 12:
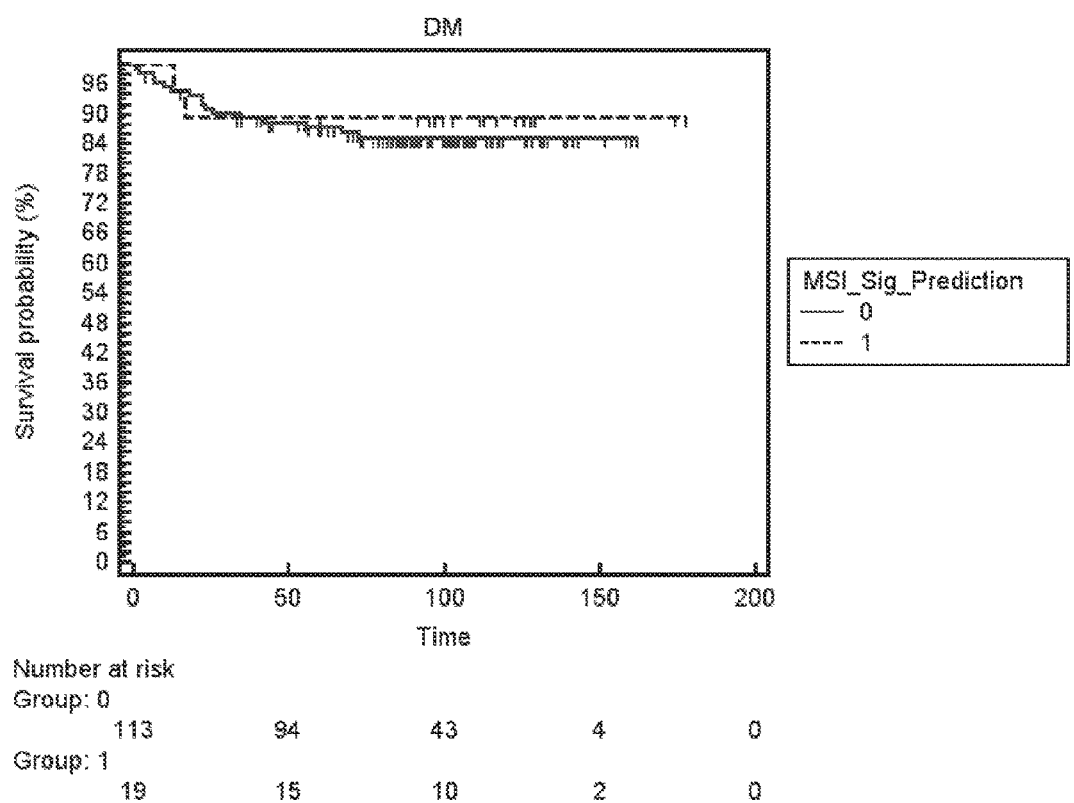

FIG. 12. 19 patients who were MSI-like as determined by the 64-gene signature but not by IHC/PCR method, tend to have a better outcome than MSS patients.

EXAMPLES

Example 1

Materials and Methods
Patients and Tumor Samples

Samples used for development of the colon molecular subtype (CMS) classifier (n=188) were prospectively collected between 1983 and 2002 at The Netherlands Cancer Institute, Amsterdam (NKI), the Leiden University Medical Center (LUMC) and the Slotervaart General Hospital in the Netherlands. Samples for the validation set of patients (n=208) were prospectively collected at the Institut Catala d'Oncologia in Barcelona, Spain, between 1996 and 2004. Clinical and pathological data were extracted from the medical records and centrally reviewed for the purpose of this study. Rectal cancer patients underwent total mesorectal excision (TME) controlled surgery. Patients were staged according to the TNM AJCC staging system and monitored for relapse (development of distant metastases or locoregional recurrence), and overall survival (median follow-up time of 65.1 months). Eighty-four percent of the samples did not receive adjuvant chemotherapy. The study was approved by the Medical Ethical Board of the participating medical centers.

Gene Expression Analysis

RNA isolation, labelling and hybridization to whole genome oligonucleotide high density microarrays followed procedures similarly as previously described [Roepman et al, 2009. Clin Cancer Res 15: 284-90]. Samples were hybridized against a colon cancer reference pool, consisting of primary tumor tissue from 44 CRC patients. Raw fluorescence intensities were quantified and normalized using Agilent Feature Extraction software according to the manufacturers' protocols and imported into R/Bioconductor (http://www.bioconductor.org/) for further analysis.

Mutational and MSI Analysis

Mutations in BRAF V600, KRAS codons 12, 13 and 61, and PIK3CA exons 9 and 20 were assessed in cDNA by means of direct sequencing of PCR products using primers with M13 tails after RT-PCR. (ServiceXS BV, Leiden, Netherlands). Mutation analysis in K-ras was performed by sequencing the whole gene to detect the activating mutations in codon 12 and 13 (most common) and 61. The primers used were 5'-aggcctgctgaaaatgaxtg (left primer) and 5'-tggtgaatatcttcaaatgatttagt-M13 (right primer). The product size was 297 bp. For PI3-Kinase, mutations were analyzed in two previously reported "hotspot" regions in exons 9 and 20, corresponding to the accessory (helical) and catalytic domains of PIK3CA, respectively. For Exon 9, the primers used were 5'-ccacgcaggactgagtaaca (left primer) and 5'-ggccaatcttttacccaagca-M13 (right primer). For Exon 20, the left primer used was 5'-tgagcaagaggctttggagt) and the right primer was 5'-agtgtggaatccagagtgagc-M13). B-Raf mutations were analyzed in exon 15 after amplification of cDNA to detect a V600E activating mutation. Primers used were (primer 1) 5'-tgatcaaacttatagatattgcacga and (primer 2) 5'-tcatacagaacaattccaaatgc. Amplified products were purified using a Macherey-Nagel NucleoFast® purification kit and checked on gel for size and yield. Approximately 16-20 ng of each product was used in a reverse sequence reaction using the M13 primers. The Mutation Surveyor Software was used for Genotyping analysis. BRAF, KRAS and PI3K mutation status were determined for 179, 177 and 176 samples, respectively.

To determine the microsatellite status, 5 μm slides were immunohistochemically (IHC) stained for the markers MLH1 and PMS2 using standard protocols to identify MSI and MSS patients. Ninety of 188 samples could be scored for their MSI status by IHC. Alternatively, for all samples we have used the expression levels of MLH1 and PMS2 as measured on the microarray as a surrogate marker for their MSI/MSS status. Analysis on the first 90 samples indicated that the expression levels of MLH1 correlated well with the IHC status, justifying the use of the surrogate marker.

Unsupervised Clustering of Tumor Samples

Unsupervised hierarchical clustering (HC) as presented previously [Salazar et al, 2010. J Clin Oncol 28:15s, abstr TPS199] was performed across 33,834 gene probes that showed a significant variation in log-ratio measurements across the 188 analyzed colon tumor samples. The HC was based on euclidean distance measurement using complete linkage.

Alternatively, a k-means (k=3) clustering method (kMC) using a 5-fold cross validation (CV) procedure was used to determine how often samples were classified together into one of three unsupervised groups. In each 5-fold CV iteration, 150 samples were randomly selected and clustered in three groups one hundred times, each time based on 500 randomly selected genes, and the majority vote was chosen as CV-outcome. The 5-fold CV procedure was repeated a hundred times and resulted in an ABC classification likelyhood for each of the 188 tumor samples. The final k-means classification was based on the highest likely-hood scores.

Identification of Subtype Specific Gene Profiles

A 5-fold cross validation (CV) procedure within a leave-one out (LOO) CV loop was used for identification of subtype specific gene profiles. Within each 5-fold CV step, genes were scored for their association with the ABC clusters using a Student's T-test based on a randomly selected four-fifth of the training samples (also excluding the LOO-sample) and using a 3-way comparison in which A-type samples were compared with B-type, A-type with C-type, and B-type with C-type. Genes differentially regulated in each of the subtypes were selected by combined the three T-test statistics, and an A-type, B-type and C-type specific gene profile was identified. Performance of the three constructed gene profiles was tested on the remaining one-fifth of the training samples (again excluding the LOO-sample) using a nearest centroid classification method. For each LOOCV loop, the 5-fold CV procedure was repeated one hundred times and the gene profiles with a significant performance on the test samples were combined into three ABC profiles and cross validated on the LOO-sample. Finally, the LOOCV results were combined into three distinct gene profiles specific for A-type, B-type and C-type tumor samples, and the samples were classified using a nearest-centroid based classification method.

Results
Identification of Three Robust Unsupervised Subgroups

A set of 188 colon cancer primary tumors was analyzed for their full-genome gene expression patterns. Clustering based on full-genome expression patterns resulted in three subgroups with different outcome and served as a starting point for the development of a prognosis related gene profile called ColoPrint [Salazar et al, 2010. J Clin Oncol 28:15s, abstr TPS199]. The molecular characteristics and percentage of patients in these three unsupervised colon tumor groups were reminiscent of the molecular CpG island methylation phenotype subtypes that are characterized by MSI, BRAF mutation, and methylation status described by others [Poynter et al, 2008. Cancer Epidemiol Biomarkers Prev 17: 3208-15].

Full-genome hierarchical clustering of the 188 colon tumors resulted in three distinct tumor groups that were associated with disease progression and MSI and BRAF mutation status (FIG. 1A). Since this grouping was based on only a single hierarchical clustering across all significantly measured gene probes, we first investigated the stability of the unsupervised three-group classification. A k-means (k=3) clustering method using a 5-fold cross validation (CV) procedure was used to determine how often samples were classified together into one of three unsupervised groups.

Although the hierarchical clustering (HC) indicated three distinct sample groups, a substantial number of samples (n=37, 19.7%) showed a difference with k-means clustering (kMC) outcome (FIG. 1B). These differences indicated that the original HC might not be as stable as would be expected from the visual inspection, a phenomenon that has previously been known for HC based subtyping in breast cancer [Pusztai et al, 2006. Oncologist 11: 868-77]. As such, the development of a classification model based on subtype specific gene profiles is preferred over binary clustering methods.

Development of Subtype Specific Gene Profiles and a Colon Molecular Subtype (CMS) Classifier Samples with a concordant classification between HC and kMC (FIG. 1) were used for construction of subgroup specific gene profiles and comprised of 44 samples classified as A-type 85 as B-type, and 22 as C-type. A 5-fold CV procedure within a leave-one out (LOO) CV loop was used for identification of subtype specific gene profiles and to score the classification performance compared to the initial clustering outcomes. LOOCV classifications of the 151 training samples were high correlative with the clustering methods (AUC of 0.987, 0.988 and 0.985 for A, B and C subtypes, respectively) and indicated that the full-genome based unsupervised clustering could be accurately reproduced using three dedicated gene profiles that contained only a small number of genes.

Finally, the LOOCV gene profiles were combined into three distinct gene profiles by selection of the genes that were used in all 151 LOOCV iterations.

As such, the gene sets with which the final nearest-centroid based colon molecular subtypes (CMS) classifier was constructed consisted of the most robustly subtype associated genes. The A-type specific gene profile consisted of 32 genes (35 unique probes), the B-type of 53 genes (61 unique probes) and the C-type of 102 genes (104 unique probes) (Table 1). Classification of all the 188 studied colon tumor samples by the CMS classifier resulted in 65 samples (35%) to be classified as A-type, 98 (52%) as B-type and 25 (13%) as C-type colon tumors (FIG. 2). As expected, the CMS results of the 151 training samples showed a very high concordance (97%) with the original full-genome HC and kMC classifications and only 4 samples were classified differently based on the gene profiles. Analysis of the 37 samples that were discordant between the unsupervised clustering methods, and which were therefore excluded from profile development, indicated that CMS classification was more similar to the kMC classification (60% concordance) than to the HC outcome (39% concordance).

Molecular subtype outcome is associated with MSI and BRAF mutations Ninety of the 188 patients could be scored for microsatellite status by standard IHC procedure. Of the 90 patients with known microsatellite status 15 were MSI. Interestingly, MSI status was unequally distributes across the different subtypes with 14 of the 15 MSI patients classified as A-type (Table 2). None of the B-type samples and only one C-type sample showed a MSI phenotype. To be able to expand the comparison of the CMS outcome with MSI status across all 188 samples, we have used the expression levels of MLH1 and PMS2 as measured on the microarray as a surrogate marker for their MSI/MSS status. RNA expression levels of MLH1 and PMS2 was significant associated with known MSI status (MLH1, correlation 0.64, Wilcoxon P=5.7 e-06; PMS2, corr 0.40, P=2.5 e-5). Scoring of MSI status based on RNA levels was very similar to the standard procedure using IHC (Chi-Square p<0.0001, Cohen's Kappa 0.74) justifying the use of MLH1 and PMS2 as surrogate MSI markers.

Using the above described expression markers for microsatellite status, all 188 tumor samples were classified as MSI or MSS (Table 2). Forty-three tumors (23%) showed a MSI phenotype based on the gene expression markers of which 33 were classified as A-type, only 2 as B-type and 8 as C-type colon cancer. These results indicated a significant association of the CMS classification and the microsatellite phenotype using both detection measurements (based on RNA levels, 1.9 e-12, n=188; based on standard IHC, 4.9 e-5, n=90). The occurrence of MSI was high in A-type tumors (51% and 37%, respectively), moderate in C-type tumors (23% and 10%) and very low in the largest B-type tumor class (2% and 0%) (Table 2).

Next, we investigated the association of molecular classification by CMS with activating mutation status of EGFR pathway associated genes BRAF, KRAS and PIK3CA. A-type is BRAFmut enriched and B-type contains MSS only and BRAF wildtype only (Table 3). The C-Type has a high slightly higher concentration of patients with BRAF mutations. KRAS and PI3K mutation frequency was similar in all three groups.

Molecular Subtype Classification is Associated with Prognosis

Patients with subtype A showed a relatively good prognosis whereas patients with subtype C had a poor outcome and a 50% risk to experience a relapse of their disease. Most patients fell into the intermediate prognosis cluster, subtype B. The subgroups were prognostic for the development of distant metastasis, relapse of any kind (local, regional or distant) and overall survival (FIG. 3).

Example 2

Independent Validation

To validate the CMS in an independent patient cohort, the profile was applied to 208 patients treated at the Institute Catalan Oncologia, Barcelona (Spain). Patient Information, clinical and pathological information and MSI, KRAS-, BRAF- and PI3K-muation status was available for nearly all patients. The results of the validation are summarized in FIG. 4.

Using the molecular characteristics described above, the independent validation confirms the difference of the Molecular subtypes. The A-type is enriched for MSI-H patients (p<0.000) and patients with BRAF mutations (p=0.03). Patients of the A-type have an excellent prognosis to stay disease-free with a 5-year DMFS chance of 97.1% (95% 91.5-100) while the B-type patients have a intermediate prognosis (5-year DMFS 80.2%) and the C-type a very poor prognosis (5-year DMFS 58.3%).

Example 3

The benefit of chemotherapy in colon cancer in the adjuvant setting is limited. Stage II patients have a maximal benefit of 3-4% while stage III patients have a relative benefit of 13-20%. Even more disappointing: many targeted therapies have shown no benefit in stage III patients although they have helped patients with metastatic colon cancer. Recent large Phase III studies have failed to show benefit for stage III patients from the treatment with Avastin (AVANT Study and NSABP C-08 study) or Erbitux. These results indicate that a better patient stratification is required to identify those patients who might benefit and that there is still a high need for better targeted therapies.

The identification of high-risk patients is the first step to identify those patients who are in need of treatment. The molecular subtype signature can identify a small very high risk group who should receive aggressive treatment. Moreover, the signature to identify these C-type patients also contains many genes that are potential targets for new drug and therefore might be useful in guiding new clinical studies (Table 1).

For example, the secreted protein acidic and rich in cysteine/osteonectin/BM40, or SPARC, is one of the genes overexpressed in the C-type patients (FIG. 5). SPARC is a matrix-associated protein that elicits changes in cell shape, inhibits cell-cycle progression, and influences the synthesis of extracellular matrix (ECM). SPARC expression levels were associated a risk of recurrence and a more aggressive phenotype. SPARC overexpression may correlate with response to nab-paclitaxel, as shown in early phase clinical studies. If confirmed in larger studies, treatment with nab-paclitaxel may convert a poor prognosis SPARC-positive patient population into a group with better clinical outcomes [Desai et al. 2009. Transl Oncol 2: 59-64].

Other potential drug targets of the signature are listed below:

Janus kinases (JAK) are a small family of receptor-associated kinases, that together with signal transducers and activators of transcription (STAT), provide a rapid signalling pathway for cytokines. Many protein tyrosine kinases (PTK), including Janus kinase 3 (JAK3) have been recently identified as potential drug targets to treat diverse diseases including inflammation and cancer. The wealth of structural information currently available for protein kinase-inhibitor complexes facilitates the structure-based design of novel kinase inhibitors and quite a number of companies are developing selective JAK3 inhibitors.

Claudins (like CLDN5) are integral membrane proteins and components of tight junction strands. Tight junction strands serve as a physical barrier to prevent solutes and water from passing freely through the paracellular space between epithelial or endothelial cell sheets. Over-expression of claudin is observed frequently in malignant tumors. First results with monoclonal antibodies indicate that claudin targeting may be a novel strategy for inhibiting some tumor metastases. CLDN5 is over-expressed in C-type patients.

FLT4, or fms-related tyrosine kinase 4 or VEGFR-3, encodes a tyrosine kinase receptor for vascular endothelial growth factors C and D. The protein is thought to be involved in lymphangiogenesis and maintenance of the lymphatic endothelium. Multiple small-molecule, multi-targeted receptor tyrosine kinase (RTK) inhibitor (like e/g. Sunitinib, pazopanib, CEP 7055, KRN-951, telatinib, sorafenib are developed and tested in various cancers. The VEGF-receptor is also indirectly involved in response to the anti-VEGF antibodies that are currently in clinical use (e.g Bevacuzimab). FLT4 is up-regulated in C-type patients.

FGFR1 is a member of the fibroblast growth factor receptor (FGFR) family and consists of an extracellular region, composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. Recent studies have shown that Brivanib, a selective dual inhibitor of FGF and VEGF signaling, demonstrates antitumor activity in a broad range of xenograft models. Pazopanib is a potent and selective multi-targeted receptor tyrosine kinase inhibitor that might inhibit also FGFR1. In C-type patients, this kinase is overexpressed.

MAP3K3 encodes a mitogen-activated protein kinase kinase kinase and its catalytic domain is closely related to those of several other kinases. This protein directly regulates the stress-activated protein kinase (SAPK) and extracellular signal-regulated protein kinase (ERK) pathways by activating SEK and MEK1/2 respectively. Multiple MAP-Kinase inhibitors are currently in clinical studies to study their potential to inhibit cancer progression. In C-type patients, MAP3K3 is over-expressed and might lead to better sensitivity to kinase inhibitors.

PDGFRB, platelet-derived growth factor receptor, is a cell surface tyrosine kinase receptor for members of the platelet-derived growth factor family and investigated as new drug targets in cancer (e.g. dasatinib, sunitinib, pazopanib, axitinib, KRN-951, tandutinib, imatinib, sorafenib, becaplermin). The receptor is over-expressed in C-type patients indicating that inhibition of the receptor function might inhibit cancer progression. Tubulin 6 (TUBB6), a β-tubulin, is one of the proteins that make up microtubules. Microtubules serve as structural components within cells and are involved in many cellular processes including mitosis, cytokinesis, and vesicular transport. Tubulins are targets for anticancer drugs like Taxol, Tesetaxel and the "Vinca alkaloid" drugs such as vinblastine and vincristine. The tubulin is over-expressed in C-type patients.

BCL2L14 belongs to the BCL2 protein family. BCL2 family members form hetero- or homodimers and act as anti- or pro-apoptotic regulators that are involved in a wide variety of cellular activities. Over-expression of this gene has been shown to induce apoptosis in cells. In C-type patients this gene is down-regulated.

XRCC2 encodes a member of the RecA/Rad51-related protein family that participates in homologous recombination to maintain chromosome stability and repair DNA damage. This gene is involved in the repair of DNA double-strand breaks by homologous recombination and it functionally complements Chinese hamster irs1, a repair-deficient mutant that exhibits hypersensitivity to a number of different DNA-damaging agents. A naturally occurring genetic variant of human XRCC2 confers increased resistance to cis-platin-induced DNA damage, indicating that this gene is essential for the response to cisplatin. XRCC2 is downregulated in C-type patients which might lead to increased sensitivity to cisplatin-induced DNA damage.

Example 4

The benefit of chemotherapy on subtypes A, B and C was investigated by survival analysis (DMFS rate at 3 years, 5 years and/or 10 years) on a total set of 757 colon samples. Thirty-four percent of these patients had received adjuvant chemotherapy after surgery while the other patients had received no further therapy. Analysis of survival on the different colon subtypes between the treated and non-treated patients was used to determine the benefit of the therapy (see FIG. 6).

Analysis on all patients showed the highest benefit of chemotherapy on C-type patients with a positive benefit of +6.3% 10 years DMFS for C-type versus a negative benefit of −1.5% and −9.9% for A-type and B-type patients A much stronger benefit of chemotherapy was observed for stage 3 patients with a subtype C colon tumor (+29.3% 10 years DMFS), but importantly also for B-type patients (+13%). For A-type stage 3 patients, a negative benefit of chemotherapy was observed (−6.1%).

Interestingly, analysis on stage 2 samples showed a benefit of chemotherapy on patients with a subtype A colon tumor (+16.9% 10 years DMFS), compared to B-type (−3.5%) and C-type (+0.1%) stage 2 patients. However, the numbers of treated stage II patients was small.

Example 5

Materials and Methods

To develop a microsatellite stability classifier, 276 fresh frozen tumor samples from patients with colorectal cancer were collected as a training set. In the training set, 5 µm slides were immunohistochemically stained for the markers MLH1 and PMS2 using standard protocols to identify MSI-high (MSI-H) patients. In total, 29 patients were identified as MSI-H in the training set (n=29 MSI, n=247 MSS). The validation study was performed on 132 tumor samples (n=132). All of 132 patients were stage 2 patients. In the validation study, the MSI status was determined by PRC amplification of six microsatellite DNA regions from paired normal and tumor tissues, and products were resolved on denaturing polyacrylamide sequencing gels. The stability of each microsatellite was scored according to the absence (stable) or the presence (unstable) of mobility-shifted bands or additional bands in tumor DNA compared with normal DNA. Two microsatellites contained mononucleotide sequences, BAT26 and SIT2, and four contained CA repeats, D21S415, D21S1235, D12S95, and D4S2948 (Murphy et al. 2006. J Mol Diagn 8: 305-11).

RNA isolation, amplification, labeling, hybridization to Agilent high density 44 k oligonucleotide microarrays and data processing were performed as described in Example 1. Since all samples contained at least 40% tumor cells we assumed that they were informative for tumor cell status. The reference comprised a pool of 44 colorectal cancer specimens and were processed and labeled in the same manner as test samples.

Normalized gene expression ratios for every hybridization were combined to produce a single gene expression profile per patient, using Matlab software (MathWorks, Inc, Natick, Mass.). To identify a gene signature that characterizes the gene expression pattern associated with MSI-H status, we used a 10-fold cross validation procedure that was repeated a thousand times to generate a robust gene selection. Within the training procedure with gene expression data of 276 patients (n=276), genes were ranked by the p-values from a Student T-test between (1) tumors identified as MSI-H (n=29) and (2) tumors not identified as MSI-H (n=247). The optimal number of signature genes was selected to reach a maximal overall accuracy. The selected set of optimal gene probes was used for construction of a nearest centroid based classification method to score all tumor samples for their correlation with the MSI-H status signature. Samples were classified within the MSI-H-like group if their signature score exceeded a pre-defined optimized threshold. The threshold for the signatures was set so that the classification had the highest average of sensitivity and specificity.

The signature was validated with gene expression data of 132 patients (n=132, n=31 MSI, n=101 MSS). Readout of the signature scores by the nearest centroid classifier methods was done in a similar fashion as used in the training procedure. Samples were classified within the MSI-H-like group if their signature score exceeded a pre-defined optimized threshold.

Results

Using a 10-fold cross validation procedure, a set of 41 genes (Table 4) were identified that can separate MSI and MSS samples with a sensitivity of 96.6% (28/29) and a specificity of 92.7% (229/247) (FIG. 7). Enriched function analysis with DAVID (Huang et al. 2009. Nat Protoc 4: 44-57.3) indicated that several of the proteins encoded by the genes in the signature are localized in nucleus and are involved in nucleic acids binding. This is consistent with the underlying biology that MSI phenotype is caused by deregulation of DNA mismatch repair (MMR) genes (Soreide et al. 2006. Br J Surg 93: 395-406).

FIG. 8 shows the prognostic value (p=0.08) of the signature in stage 2 colorectal cancer patients (n=215).

Example 6

Materials and Methods

The materials and methods used in these experiments were as described in Example 5.

Results

Using a microarray proprietary to Agendia, which comprises a subset of the 44 k gene probes, a 10-fold cross validation procedure was performed and repeated a thousand times. A list of 63 genes (Table 5) was developed and it resulted in similar performance: a sensitivity of 93.1% (27/29), a specificity of 87.9% (217/247) and overall accuracy 88.4% (244/276).

The prognostic value of the 63-genes signature in stage 2 colorectal cancer patients (n=215) was p=0.06, HR=2.38, 95% CI 1.15-4.93.

The prognostics value of the 63-genes signature was further validated on 320 samples from stage 2 patient from five different patient cohorts. The 63-genes signature showed significant prognostic value (p=0.015, HR=3.33, 95% CI 1.66-6.69) (FIG. 9).

The 63 genes in the 63 gene signature were randomly combined. As is shown in FIG. 10, a minimal number of 2 genes can already achieve above 70% overall accuracy.

A marker of MSI status, MLH1, was added to the 63 genes in the MSI signature to generate a 64 genes signature. This 64-genes signature was validated on 132 samples from stage 2 patients whose MSI status were known. In this set of samples, the sensitivity was 90.3% (28 out of 31 MSI-H), and the specificity was 83.2% (84 out of 101 MSI-L or MSS).

The prognostic value of the 64-genes signature was further validated on 320 samples from stage 2 patients from five different patient cohorts. The 64-genes signature showed significant prognostic value (p=0.017, HR=3.27, 95% CI 1.62-6.59) (FIG. 11).

Within the 320 stage 2 patients, 19 patients were identified who were MSI-like by 64-gene signature but not by IHC/PCR method. These patients tend to have a better outcome than normal MSS patients (FIG. 12) and thus might indeed be MSI-like patients. However, the small sample size (n=19) did render a significant statistical result (p=0.69).
Table 1

TABLE 1A

A-type (32 genes)

| Gene | ID | Rank UP | Rank DOWN | Ind. perf. vs profile (AUC) |
|---|---|---|---|---|
| ACADSB | NM_001609 | 10 | | 0.79 |
| ARFGAP1 | NM_175609 | | 13 | 0.900 |
| AS3MT | NM_020682 | | 10 | 0.919 |
| CTSF | NM_003793 | | 7 | 0.804 |
| DEPDC1 | NM_017779 | 9 | | 0.768 |
| DKFZp547K054 | AL390175 | | 9 | 0.901 |
| DLG7 | NM_014750 | 5 | | 0.778 |
| ECHS1 | NM_004092 | 8 | | 0.837 |
| EIF4A2 | NM_001967 | 11 | | 0.782 |
| FCGRT | NM_004107 | | 5 | 0.862 |
| FHOD3 | NM_025135 | | 3 | 0.809 |
| HSPA4L | NM_014278 | 1 | | 0.903 |
| KNTC2 | NM_006101 | 6 | | 0.801 |
| LARP6 | NM_018357 | | 4 | 0.798 |
| ME1 | NM_002395 | 4 | | 0.828 |
| MREG | NM_018000 | 12 | | 0.821 |
| NIPA1 | NM_144599 | 13 | | 0.816 |
| NRXN2 | NM_138732 | | 14 | 0.902 |
| NUDT6 | NM_007083 | 3 | | 0.872 |
| PAPLN | NM_173462 | | 12 | 0.808 |
| PRC1 | NM_199413 | 7 | | 0.790 |
| RARA | NM_000964 | | 16 | 0.826 |
| RGN | NM_004683 | | 8 | 0.847 |
| RP4-691N24.1 | NM_025176 | | 2 | 0.792 |
| SLC7A11 | NM_014331 | 2 | | 0.794 |
| SMARCC2 | NM_139067 | | 11 | 0.806 |
| SNX21 | NM_001042633 | | 15 | 0.902 |
| SORBS1 | NM_015385 | | 6 | 0.904 |
| SRPX2 | NM_014467 | | 1 | 0.838 |
| TIAL1 | NM_003252 | 14 | | 0.768 |
| URM1 | NM_030914 | | 18 | 0.819 |
| ZNF167 | NM_025169 | | 17 | 0.797 |

TABLE 1B

B-type (53 genes)

| Gene | ID | Rank UP | Rank DOWN | Ind. perf. vs profile (AUC) |
|---|---|---|---|---|
| ACSL6 | NM_001009185 | 14 | | 0.849 |
| AMACR | NM_014324 | 18 | | 0.855 |
| ARFGEF2 | NM_006420 | 36 | | 0.872 |
| AXIN2 | NM_004655 | 9 | | 0.861 |
| BG114486 | BG114486 | 1 | | 0.949 |
| C13orf18 | NM_025113 | 10 | | 0.852 |
| C20orf111 | NM_016470 | 29 | | 0.893 |
| C20orf142 | NM_001080472 | 24 | | 0.904 |
| C20orf43 | NM_016407 | 30 | | 0.874 |
| CEBPA | NM_004364 | 20 | | 0.872 |
| CEP250 | NM_001035518 | 42 | | 0.833 |
| COBLL1 | NM_014900 | 45 | | 0.807 |
| CTSL2 | NM_001333 | 17 | | 0.849 |
| CXorf56 | NM_022101 | 44 | | 0.837 |
| DDC | NM_000790 | 8 | | 0.836 |
| EPOR | NM_000121 | | 8 | 0.801 |
| FANCF | NM_022725 | 38 | | 0.822 |
| GGH | NM_003878 | 12 | | 0.831 |
| GPSM2 | NM_013296 | 25 | | 0.815 |
| HNF4A | NM_000457 | 31 | | 0.894 |
| IFT52 | NM_016004 | 43 | | 0.893 |
| KCTD1 | NM_198991 | | 5 | 0.858 |
| KIF3B | NM_004798 | 35 | | 0.871 |
| LOC388610 | NM_001013642 | | 1 | 0.826 |
| MAPRE2 | NM_014268 | | 7 | 0.833 |
| MOCS3 | NM_014484 | 40 | | 0.898 |
| NCOA6 | NM_014071 | 28 | | 0.886 |
| PARD6B | NM_032521 | 21 | | 0.871 |
| PIGU | NM_080476 | 41 | | 0.915 |
| PIWIL2 | NM_018068 | 37 | | 0.801 |
| PLA2G12B | NM_032562 | 4 | | 0.892 |
| PLAGL2 | NM_002657 | 13 | | 0.943 |
| PLK2 | NM_006622 | | 3 | 0.852 |
| POFUT1 | NM_172236 | 19 | | 0.914 |
| PRDX5 | NM_012094 | 22 | | 0.866 |
| PSMA7 | NM_002792 | 32 | | 0.893 |
| PTPRO | NM_030667 | 6 | | 0.794 |
| QPRT | NM_014298 | 3 | | 0.905 |
| RAMP1 | NM_005855 | | 2 | 0.812 |
| RBP2 | NM_004164 | 15 | | 0.840 |
| RNF43 | NM_017763 | 7 | | 0.902 |
| RP11-78J21.1 | NM_001011724 | 34 | | 0.882 |
| SEPHS2 | NM_012248 | 23 | | 0.841 |
| SLC41A1 | NM_173854 | | 6 | 0.809 |
| SLC5A6 | NM_021095 | 26 | | 0.888 |
| SLC6A4 | NM_001045 | 16 | | 0.914 |
| THC2644861 | THC2644861 | 39 | | 0.877 |
| THC2669157 | THC2669157 | 2 | | 0.888 |
| TP53RK | NM_033550 | 27 | | 0.899 |
| TRIB2 | NM_021643 | | 4 | 0.895 |
| TSPAN6 | NM_003270 | 11 | | 0.921 |
| VAPB | NM_004738 | 33 | | 0.912 |
| VAV3 | NM_006113 | 5 | | 0.911 |

TABLE 1C

C-type (102 genes)

| Gene | ID | Rank UP | Rank DOWN | Ind. perf. vs profile (AUC) |
|---|---|---|---|---|
| AEBP1 | NM_001129 | 8 | | 0.913 |
| AK021531 | AK021531 | 43 | | 0.866 |
| ANKRD35 | NM_144698 | 66 | | 0.898 |
| ASPM | NM_018136 | | 6 | 0.827 |
| BASP1 | NM_006317 | 9 | | 0.914 |
| BCL2L14 | NM_030766 | | 19 | 0.836 |
| BNC2 | NM_017637 | 29 | | 0.918 |
| C14orf139 | BC008299 | 74 | | 0.891 |
| C1orf198 | NM_032800 | 76 | | 0.828 |
| C1QTNF6 | NM_031910 | 48 | | 0.896 |
| CALD1 | NM_033138 | 44 | | 0.882 |
| CD248 | NM_020404 | 23 | | 0.944 |
| CLDN5 | NM_003277 | 27 | | 0.881 |
| CLEC11A | NM_002975 | 63 | | 0.903 |
| COL18A1 | NM_030582 | 51 | | 0.920 |
| COL1A2 | NM_000089 | 11 | | 0.880 |
| COL5A1 | NM_000093 | 14 | | 0.892 |
| COL5A2 | NM_000393 | 3 | | 0.873 |
| COL6A1 | NM_001848 | 10 | | 0.893 |
| COL6A3 | NM_004369 | 32 | | 0.930 |
| COX7A1 | NM_001864 | 41 | | 0.918 |
| CPSF6 | NM_007007 | | 20 | 0.828 |
| CRYAB | NM_001885 | 25 | | 0.886 |
| CXCL12 | NM_000609 | 26 | | 0.832 |
| DCN | NM_001920 | 7 | | 0.869 |
| DIAPH3 | NM_030932 | | 1 | 0.877 |
| DTX3 | NM_178502 | 49 | | 0.845 |
| EFHA2 | NM_181723 | 54 | | 0.873 |
| ELMO1 | NM_014800 | 80 | | 0.860 |

TABLE 1C-continued

C-type (102 genes)

| Gene | ID | Rank UP | Rank DOWN | Ind. perf. vs profile (AUC) |
|---|---|---|---|---|
| EVL | NM_016337 | 31 | | 0.870 |
| FAM20C | AL390147 | 59 | | 0.887 |
| FBLN1 | NM_006485 | 4 | | 0.895 |
| FBXO17 | AK021860 | 62 | | 0.819 |
| FBXO5 | NM_012177 | | 7 | 0.873 |
| FES | NM_002005 | 69 | | 0.873 |
| FGFR1 | NM_023111 | 42 | | 0.904 |
| FLT4 | NM_002020 | 77 | | 0.847 |
| FSTL1 | NM_007085 | 15 | | 0.869 |
| GGTLA1 | NM_004121 | 55 | | 0.887 |
| GPSM1 | NM_015597 | 33 | | 0.842 |
| GPSM3 | NM_022107 | 72 | | 0.882 |
| GPX7 | NM_015696 | 40 | | 0.877 |
| HTRA1 | NM_002775 | 12 | | 0.900 |
| IGFBP5 | NM_000599 | 58 | | 0.842 |
| JAK3 | NM_000215 | 45 | | 0.864 |
| JAM2 | NM_021219 | 53 | | 0.857 |
| KIAA1442 | XM_938882 | 67 | | 0.895 |
| KIAA1602 | NM_020941 | 79 | | 0.876 |
| LAMB2 | NM_002292 | 38 | | 0.915 |
| LAMC1 | NM_002293 | 56 | | 0.892 |
| LGALS1 | NM_002305 | 24 | | 0.890 |
| LOC338328 | NM_178172 | 65 | | 0.914 |
| LOC387763 | BC052560 | 28 | | 0.823 |
| LOXL1 | NM_005576 | 13 | | 0.898 |
| MAP3K3 | NM_203351 | 71 | | 0.928 |
| MC1R | NM_002386 | 37 | | 0.864 |
| MGP | NM_000900 | 5 | | 0.878 |
| MSN | NM_002444 | 17 | | 0.896 |
| MXRA8 | NM_032348 | 6 | | 0.925 |
| NDUFA10 | NM_004544 | | 12 | 0.856 |
| NDUFAB1 | NM_005003 | | 15 | 0.869 |
| NID2 | NM_007361 | 50 | | 0.857 |
| NIPSNAP1 | NM_003634 | | 3 | 0.800 |
| NPC2 | NM_006432 | 73 | | 0.867 |
| OBSL1 | XM_051017 | 30 | | 0.861 |
| ORC6L | NM_014321 | | 5 | 0.851 |
| PA2G4 | NM_006191 | | 11 | 0.842 |
| PCOLCE | NM_002593 | 39 | | 0.860 |
| PDGFRB | NM_002609 | 19 | | 0.871 |
| PDLIM4 | NM_003687 | 64 | | 0.903 |
| PGF | NM_002632 | 70 | | 0.837 |
| POLE | AF128541 | | 21 | 0.796 |
| PPARA | L02932 | | 8 | 0.811 |
| RABL3 | NM_173825 | | 14 | 0.841 |
| RARRES2 | NM_002889 | 16 | | 0.853 |
| RFC4 | NM_181573 | | 10 | 0.865 |
| RNF207 | NM_207396 | 81 | | 0.853 |
| ROBO4 | NM_019055 | 57 | | 0.881 |
| SERPINF1 | NM_002615 | 21 | | 0.902 |
| SLC27A1 | NM_198580 | 52 | | 0.884 |
| SLIT3 | AL122074 | 36 | | 0.921 |
| SNRP70 | NM_003089 | 78 | | 0.789 |
| SNRPC | NM_003093 | | 17 | 0.858 |
| SPARC | NM_003118 | 18 | | 0.858 |
| SPBC25 | NM_020675 | | 2 | 0.873 |
| SPOCK1 | NM_004598 | 2 | | 0.904 |
| SYNCRIP | NM_006372 | | 16 | 0.865 |
| TGFB3 | NM_003239 | 47 | | 0.881 |
| THBS2 | NM_003247 | 1 | | 0.889 |
| THC2532155 | THC2532155 | 75 | | 0.803 |
| THY1 | NM_006288 | 68 | | 0.887 |
| TOM1L1 | NM_005486 | | 18 | 0.856 |
| TPM2 | NM_213674 | 22 | | 0.875 |
| TRO | NM_001039705 | 46 | | 0.913 |
| TSPYL5 | NM_033512 | 60 | | 0.902 |
| TUBB6 | NM_032525 | 20 | | 0.874 |
| VAMP5 | NM_006634 | 61 | | 0.885 |
| VWF | NM_000552 | 34 | | 0.864 |
| WISP1 | NM_003882 | 35 | | 0.903 |
| XRCC2 | NM_005431 | | 13 | 0.866 |
| ZNF367 | NM_153695 | | 4 | 0.839 |
| ZNF695 | NM_020394 | | 9 | 0.851 |

TABLE 2

Association of subtype classification with MSI status.
Microsatellite status was determined based on standard IHC procedure (n = 90) and using MLH1 and PMS2 gene expression levels (n = 188).

| | | Microsatellite phenotype | | | | | |
|---|---|---|---|---|---|---|---|
| | | Based on standard IHC* (MLH1 and PMS2 markers) | | | Based on MLH1 and PMS2 expression levels** | | |
| | | MSS | MSI | % MSI | MSS | MSI | % MSI |
| Subtype by CMS | A-type | 24 | 14 | 37% | 32 | 33 | 51% |
| | B-type | 42 | 0 | 0% | 96 | 2 | 2% |
| | C-type | 9 | 1 | 10% | 17 | 8 | 32% |
| | Total | 75 | 15 | 17% | 145 | 43 | 23% |
| | Chi-square | P = 4.9e-5 | | | P = 1.9e-12 | | |

*MSI/MSS status scored according to standard IHC procedures (MLH1 and PMS2 markers)
**MSI/MSS status scored by gene expression levels of MLH1 and PMS2 (surrogate marker)

TABLE 3

Association of subtype classification with BRAF, KRAS and PI3K activating mutation status.
Mutations in BRAF V600, KRAS codons 12, 13 or 61, and PI3KCA exons 9 or 20 were assessed by sequence analysis.

| | | Activating mutation status | | | | | | | | |
|---|---|---|---|---|---|---|---|---|---|---|
| | | BRAF | | | KRAS | | | PIK3CA | | |
| | | wildtype | mutation | % mut | wildtype | mutation | % mut | wildtype | mutation | % mut |
| Subtype by CMS | A-type | 34 | 30 | 47% | 47 | 16 | 25% | 54 | 10 | 16% |
| | B-type | 91 | 0 | 0% | 67 | 24 | 26% | 85 | 6 | 7% |
| | C-type | 19 | 5 | 21% | 15 | 8 | 35% | 17 | 4 | 19% |
| | Total | 144 | 35 | 20% | 129 | 48 | 27% | 156 | 20 | 11% |
| | Chi-square | P = 3.9e-12 | | | P = 0.67 | | | P = 0.11 | | |

INCORPORATION OF SEQUENCE LISTING

Incorporated herein by reference in its entirety is the Sequence Listing for the application. The Sequence Listing is disclosed on a computer-readable text file entitled "Sequence 294-427 PCTUS," created on Jul. 22, 2013. The sequence.txt file is 16.2 kilobyte in size.

The invention claimed is:

1. A method of detecting and treating a human colorectal cancer patient, the method comprising
   a) obtaining a sample comprising ribonucleic acid (RNA) from a colorectal cancer cell from a human colorectal cancer patient,
   b) hybridizing the RNA to an array to determine a level of RNA expression in said sample for at least two genes comprising dual specificity phosphatase 18 (DUSP18) and Smith-Magenis syndrome chromosome region, candidate 7-like (SMCR7L) using at least two probes having SEQ ID NOs: 2 and 6;
   c) comparing said determined level of RNA expression of the at least two genes to the median background-subtracted level of expression of said at least two genes in a reference sample, wherein the reference sample comprises pooled RNA expression products from colorectal cancer tissue from more than ten unrelated colorectal cancer patients,
   d) detecting a sample with a decreased level of RNA expression of DUSP18 and SMCR7L compared to the reference sample, and
   e) treating the human colorectal cancer patient whose sample was identified with a decreased level of RNA expression of DUSP18 and SMCR7L with chemotherapy excluding 5-fluoro-uracil.

2. The method according to claim 1, whereby said at least two genes further comprise centrosomal protein 68 kDa (CEP68), unkempt family zinc finger-like (UNKL), potassium channel, subfamily K, member 5 (KCNK5), ring finger protein 43 (RNF43), ribosomal protein L13 pseudogene 5 (RPL22L1), Axis Inhibition Protein 2 (AXIN2), troponin C type 2 (TNNC2), Golgi-associated, gamma adaptin ear containing, ARF binding protein 2 (GGA2), ATPase, class II, type 9A (ATP9A), vav 3 guanine nucleotide exchange factor (VAV3), shroom family member 4 (SHROOM4), ZFP36 ring finger protein-like 2 (ZFP36L2), Achaete-Scute homologue 2 (ASCL2), quinolinate phosphoribosyltransferase (QPRT), shroom family member 2 (SHROOM2), pleiomorphic adenoma gene-like 2 (PLAGL2), G protein-coupled receptor 143 (GPR143), Gene indicated by gene ID HD_8_ColoP1.0_15K_02115, BC000986, BC000986, heterogeneous nuclear ribonucleoprotein L (HNRNPL), GGT7 gamma-glutamyltransferase 7 (GGT7), E1A binding protein p300 (EP300), keratin 23 (KRT23), proline rich 15 (PRR15), ependymin protein 1a (EPDR1), Rho-associated, coiled-coil containing protein kinase 2 (ROCK2), protein phosphatase 1, regulatory subunit 3D (PPP1R3D), zinc finger, SWIM-type containing 3 (ZSWIM3), C13orf18, acyl-CoA synthetase long-chain family member 6 (ACSL6), troponin T type 1 (TNNT1), tumor necrosis factor (ligand) superfamily, member 9 (TNFSF9), tripartite motif containing 7 (TRIM7), anterior gradient 2 (AGR2), sorbin and SH3 domain containing 1 (SORBS1), C20orf11, LIM domain only 4 (LMO4), tetraspanin 6 (TSPAN6), death inducer-obliterator 1 (DIDO1), C20orf43, carcinoembryonic antigen-related cell adhesion molecule 3 (CEACAM3), dynein, light chain, roadblock-type 1 (DYNLRB1), KH domain containing, RNA binding, signal transduction associated 3 (KHDRBS3), guanine nucleotide binding protein (G protein), gamma 4 (GNG4), AT rich interactive domain 3A (ARID3A), LOC157860, guanylate cyclase 2C (GUCY2C), additional sex combs like transcriptional regulator 1 (ASXL1), vanin 2 (VNN2), solute carrier family 25 (mitochondrial carrier: glutamate), member 22 (SLC25A22), O-fucosylpeptide 3-beta-N-acetylglucosaminyltransferase (LFNG), C10orf47, striatin, calmodulin binding protein 3 (STRN3), carcinoembryonic antigen-related cell adhesion molecule 5 (CEACAM5), SMAD family member 2 (SMAD2), transforming growth factor, beta receptor II (TGFBR2), Mouse Double Minute 2 (MDM2), F-box protein 34 (FBXO34), transcription factor CP2-like 1 (TFCP2L1), transcription factor 7 (TCF7) and oncoprotein induced transcript 3 (OIT3), whereby the level of RNA expression in said sample is determined by using an array comprising probes with SEQ ID NOs: 2, 6, 8, 11, 15, 18, 21, 24, 25, 35 and 42-94.

3. The method according to claim 1, further comprising converting RNA from said colorectal cancer patient into cRNA or cDNA.

4. The method according to claim 3, wherein said cRNA or cDNA is labelled.

5. The method of claim 1, whereby said at least two genes further comprise centrosomal protein 68 kDa (CEP68) and unkempt family zinc finger-like (UNKL), and wherein the level of RNA expression of said genes is determined by using a microarray comprising probes with SEQ ID NOs: 2, 6, 8 and 11.

6. The method of claim 1, whereby said at least two genes further comprise centrosomal protein 68 kDa (CEP68), unkempt family zinc finger-like (UNKL), potassium channel, subfamily K, member 5 (KCNK5), ring finger protein 43 (RNF43), ribosomal protein L22-like 1 (RPL22L1), Axis Inhibition Protein 2 (AXIN2), troponin C type 2 (TNNC2), ATPase, class II, type 9A (ATP9A), vav 3 guanine nucleotide exchange factor (VAV3), quinolinate phosphoribosyltransferase (QPRT), pleiomorphic adenoma gene-like 2 (PLAGL2), C13orf18 and AT rich interactive domain 3A (ARID3A), wherein the level of RNA expression of said genes in said sample is determined by using a microarray further comprising probes with SEQ ID NOs: 2, 6, 8, 11, 15, 17, 18, 21, 24, 25, 27, 28, 35, and 41.

7. The method of claim 1, whereby said at least two genes further comprise ariadne homolog 2 (ARIH2), mutL homolog 1 (MLH1), nucleoside diphosphate linked moiety X)-type motif 3 (NUDT3), pentatricopeptide repeat domain 2 (PTCD2), taurine up-regulated 1 (TUG1), centrosomal protein 68 kDa (CEP68), ribosomal protein L13 pseudogene 5 (RPL13P5), CDC42 small effector 1 (CDC42SE1), unkempt family zinc finger-like (UNKL), cingulin (CGN), SWI/SNF related, matrix associated, actin dependent regulator of chromatin, subfamily c, member 2 (SMARCC2), epidermal growth factor receptor (EGFR), potassium channel, subfamily K, member 5 (KCNK5), SEC22 vesicle trafficking protein B (SEC22B), pleiomorphic adenoma gene-like 2 (PLAGL2), ring finger protein 43 (RNF43), inner mitochondrial membrane peptidase-like (IMMP2L), zinc finger and BTB domain containing 20 (ZBTB20), ribosomal protein L22-like 1 (RPL22L1), calpain 1 (CAPN1), synaptojanin 2 (SYNJ2), Axis Inhibition Protein 2 (AXIN2), troponin C type 2 (TNNC2), subunit of the oligosaccharyltransferase complex (STT3A), quinolinate phosphoribosyltransferase (QPRT), vav 3 guanine nucleotide exchange factor (VAV3), ribosomal protein L15 (RPL15), C13orf18, BC035247, Family With Sequence Similarity 44, Member A (FAM44A), tripartite motif containing 44 (TRIM44), Golgi-associated, gamma adaptin ear containing, ARF binding protein 2 (GGA2); ATPase, class II, type 9A (ATP9A), slingshot protein phosphatase 2 homo (SSH2), BX119435, protein kinase, cAMP-dependent, regulatory, type II, alpha (PRKAR2A), BC010544, upstream transcription factor 1 (USF1) and AT rich interactive domain 3A (ARID3A), whereby the level of RNA expression in said sample is determined by using a microarray comprising probes with SEQ ID NOs: 1-41.

8. The method of claim 1, wherein the chemotherapy comprises at least one compound inhibiting the phosphatidylinositol 3-kinase (PI3K)-AKT-mammalian target of rapamycin (mTOR) pathway.

\* \* \* \* \*